United States Patent [19]

Ogura et al.

[11] Patent Number: 5,278,163
[45] Date of Patent: Jan. 11, 1994

[54] PYRIDAZINONE DERIVATIVES AND COMPOSITIONS FOR CONTROLLING AND/OR PREVENTING INSECT PESTS

[75] Inventors: Tomoyuki Ogura; Yasuo Kawamura; Tatsuo Numata, all of Funabashi; Toshiyuki Umehara, Saitama; Toshiro Miyake, Saitama; Hiroshi Haruyama, Saitama, all of Japan

[73] Assignee: Nissan Chemical Industries, Ltd., Tokyo, Japan

[21] Appl. No.: 956,580

[22] Filed: Oct. 5, 1992

Related U.S. Application Data

[63] Continuation of Ser. No. 522,819, May 14, 1990, abandoned.

[30] Foreign Application Priority Data

May 17, 1989 [JP] Japan .................. 1-121603
Dec. 28, 1989 [JP] Japan .................. 1-343446
Apr. 5, 1990 [JP] Japan .................. 2-90926

[51] Int. Cl.$^5$ .......................... C07D 237/16
[52] U.S. Cl. .................... 514/252; 514/247; 514/236.5; 544/238; 544/240; 544/114
[58] Field of Search ............... 514/247, 252; 544/238, 544/240

[56] References Cited

U.S. PATENT DOCUMENTS

| | | | |
|---|---|---|---|
| 4,571,397 | 2/1986 | Taniguchi et al. | 544/239 |
| 4,906,627 | 3/1990 | Nakajima et al. | 514/247 |
| 4,929,617 | 5/1990 | Leyendecker et al. | 544/238 |
| 4,945,091 | 7/1990 | Makabe et al. | 514/252 |
| 5,004,744 | 4/1991 | Weissmuller | 514/247 |
| 5,141,939 | 8/1992 | Weismuller et al. | 544/240 |

FOREIGN PATENT DOCUMENTS

1097270 5/1986 Japan .................. 514/247

OTHER PUBLICATIONS

Gymev et al Chem Abstr vol. 93 entry 114552g (1980) abstracting GB 2025416.
Synthesis, "Phase-Transfer Catalyzed N-Alkylation of 3(2H)-Pyridazinones (3-Oxo-2,3-dihydropyridazines)", Yamada et al., Aug. 1981, vol. 0039-7881/81/0832, pp. 0631-3, Georg Thieme Verlag, Stuttgart/New York.

Primary Examiner—Donald G. Daus
Attorney, Agent, or Firm—Oliff & Berridge

[57] ABSTRACT

A novel 3(2H)-pyradazinone derivative of the formula (I)

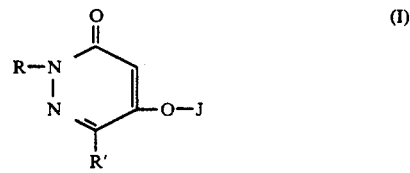

wherein, R represents an alkyl group having 1 to 4 carbon atoms substituted by a cycloalkyl group having 3 to 8 carbon atoms, an alkyl group having 1 to 4 carbon atoms substituted by a phenyl group which may be substituted or an alkyl group having 1 to 4 carbon atoms substituted by a heterocyclic group, R' represents a hydrogen atom, a halogen atom, an alkoxy group having 1 to 4 carbon atoms or a hydroxyl group having 1 to 4 carbon atoms, J represents any of various organic radicals. There is also provided a process for preparing said derivatives. These derivatives are useful as active ingredients of insecticidal, acaricidal and/or nematicidal compositions for agricultural and horticultural uses as well as of expellent compositions for pests parasitic on animals.

15 Claims, No Drawings

PYRIDAZINONE DERIVATIVES AND COMPOSITIONS FOR CONTROLLING AND/OR PREVENTING INSECT PESTS

This is a continuation of application Ser. No. 07/522,819, filed May 14, 1990, now abandoned.

BACKGROUND OF THE INVENTION

The present invention relates to novel 3(2H)-pyridazinone derivatives and insecticidal, acaricidal and nematicidal compositions and compositions for expelling pests parasitic on animals containing as an active ingredient said derivatives.

PRIOR ART

The present invention concerns EP-A-0088384, EP-A-0134439, EP-A-0183212, EP-A-0199281, EP-A-0210647, EP-A-0193853, EP-A-0232825 and EP-A-0302346. The known compounds contained in these patent publications are represented by the following general formula (II):

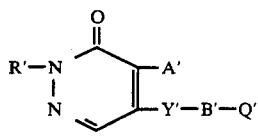

The characteristics of the compounds of these publications are, e.g., in the above formula (II): in the cases of EP-A-0088384; EP-A- 0134439, EP-A-0183212, EP-A-0199281 and EP-A-0232825, Y' represents an oxygen atom or a sulphur atom, but A' represents a substituent such as halogen; in the case EP-A-0302346, R' represents a group such as an alkyl group substituted by halogen atom. In EP-A-0193853, Y' represents nitrogen atom or oxygen atom, but A' represents a substituents such as a halogen. However, the compounds of the present invention are novel compounds which are not covered by these European patent publications.

SUMMARY OF THE INVENTION

An object of the present invention is to provide novel 3(2H)-pyridazinone derivatives which have insecticidal, acaricidal and nematicidal activities.

Another object of the present invention is to provide a process for preparing such 3(2H)-pyridazinone derivatives.

Still another object of the present invention is to provide insecticidal, acaricidal, nematicidal and molluscicidal compositions and compositions for expelling pests parasitic on animals, said compositions containing at least one of such 3(2H)-pyridazinone derivatives as an active ingredient.

Still another object of the present invention is to provide a method for controlling and/or preventing insect pests by using the above-mentioned derivatives or compositions.

Other objects of the present invention will become apparent from the description given below.

DETAILED DESCRIPTION OF THE INVENTION

The present invention relates to novel 3(2H)-pyridazinone derivatives of the formula (I);

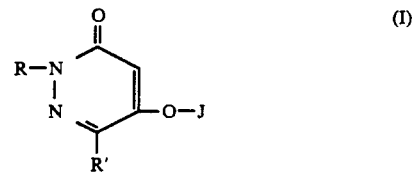

wherein
R represents an alkyl group having 1 to 4 carbon atoms substituted by a cycloalkyl group having 3 to 8 carbon atoms, an alkyl group having 1 to 4 carbon atoms substituted by a phenyl group which may be substituted or an alkyl group having 1 to 4 carbon atoms substituted by a heterocyclic group which may be substituted;

R' represents a hydrogen atom, a halogen atom, an alkoxy group having 1 to 4 carbon atoms or a hydroxyl group. J represents

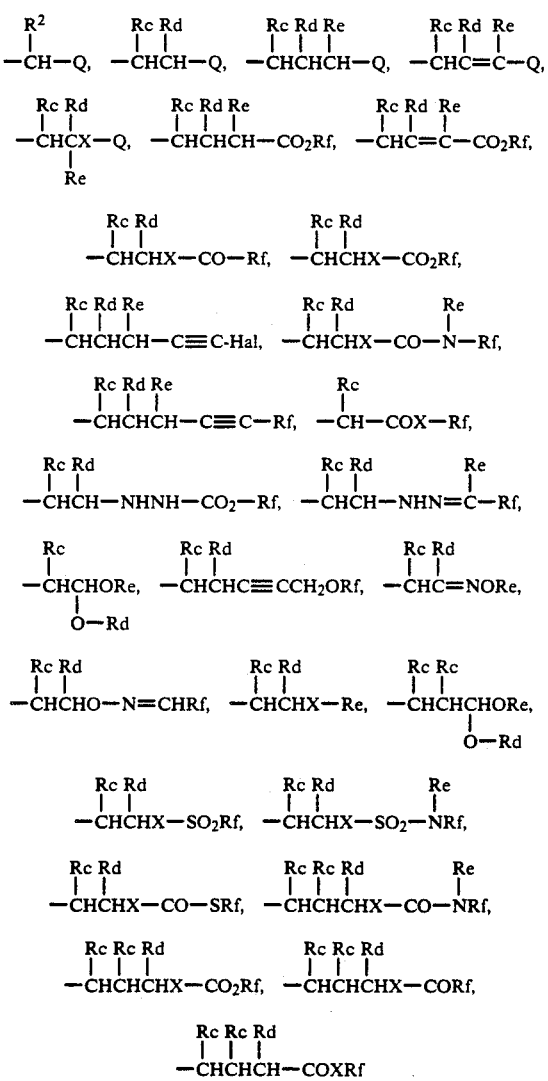

or a haloalkyl group having 1 to 3 carbon atoms in which $R^2$, Rc, Rd and Re independently represent a hydrogen atom or an alkyl group having 1 to 4 carbon atoms, Rf represents a hydrogen atom, an alkyl group having 1 to 4 carbon atoms, an alkenyl group having 2 to 8 carbon atoms, a cycloalkyl group having 3 to 8 carbon atoms, a phenyl group which may be substituted or a heterocyclic group which may be substituted, X represents —O—, —S —, —NH— or

(Rg represents an alkyl group having 1 to 4 carbon atoms), Hal represents a halogen atom, Q represents a phenyl group which may be substituted, a naphthyl group which may be substituted or a heterocyclic group which may be substituted; a process for producing said derivatives and insecticidal, acaricidal or nematicidal compositions and compositions for expelling pests parasitic on animals containing as an active ingredient one or more of said derivatives.

After intensive research, the present inventors have found that the compounds of the general formula (I) have excellent insecticidal, acaricidal, nematicidal and molluscicidal activities.

For example, the known compounds of the formula (II) have strong insecticidal, acaricidal, nematicidal and fungicidal activities and have a wide insecticidal spectrum and are excellent in prompt effectiveness. On the other hand, the compounds of the present invention are slow in effectiveness because they have activity to inhibit metamorphosis of insect pests. Moreover, the compounds of the present invention are effective, with a very low drug-concentration, on various kinds of insect pests; e.g., agricultural insect pests such as green rice leaf hopper (*Nephotettix cincticeps*), brown rice planthopper (*Nilaparvata lugens*), green peach aphid (*Myzus persicae*), diamondback moth (*Plutella xylostella*), common cutworm (*Spodoptera litura*), two-spotted spider mite (*Tetranychus urticae*), citrus red mite (*Panonychus citri*), Kanzawa spider mite (*Tetranychus kanzawai*), sanitary insect pests such as house mosquito (*Culex pipiens palens*), housefly (*Musca domestica*), German cockroach (*Blattella germanica*), ant(Formicidae), chironomid (Chironomideae), flea (Siphonaptera), lice (Anoplura) ; stored product insect pests such as maize weevil (*Sitophilus oryzae*), red flour beetle (*Tribolium castaneum*), almond moth (*Cadra cautella*); house insect pests such as termites and veterinary insect pests such as ticks, acarids, fleas, lice, flies; house mites such as (*Tyrophagus putrescentiae*), (*Dermatophagoides farinae*), (*Dermatophagoides pteronyssinus*), (*Cheyletus malaccensis*); Mollusca such as slugs and snails and the like;

In other words, the compounds of the present invention can effectively control and prevent Dictyoptera, Isoptera, Hemiptera, Lepidoptera, Coleoptera, Hymenoptera, Diptera, ticks, acari and lice.

The above-mentioned effects are described in detail in the biological examples later described.

In the substituent "J" in the above-mentioned formula (I), when Q represents a phenyl group which may be substituted, a naphthyl group which may be substituted, for example, as the following kinds of substituents: a halogen atom, an alkyl group, an alkenyl group, an alkynyl group, a cycloalkyl group, an alkoxy group, an alkenyloxy group, an alkynyloxy group, a methylenedioxy group, a halogen-methylenedioxy group, an alkylthio group, an alkenylthio group, an alkylsulfinyl group, an alkylsulfonyl group, a cycloalkyloxy group, a haloalkyl group, a haloalkoxy group, a haloalkylthio group, an alkylamino group, an alkylcarbonylamino group, a nitro group, a cyano group, a hydroxyl group, an alkylcarbonyl group, an alkoxycarbonyl group, carboxyl group, aryl group, an aryloxy group, an arylthio, an arylamino group, an arylcarbonyl group, an arylmethyleneoxy group, an aryloxymethyl group, an arylmethylenecarbonyl group, a substituted or unsubstituted pyridyloxy group, a hydroxyalkyl group, an alkylcarbonyloxyalkyl group, an alkoxyalkyl group, an alkylthioalkyl group, an alkylcarbonylalkyl group, an alkoxycarbonylalkyl group, a cyanoalkyl group, a haloalkylcarbonyl group.

In the substituent "J" of the general formula (I), when Q is a heterocyclic ring group, Q may be one of the following heterocyclic rings: e.g. thiophene, furan, pyrrole, imidazole, thiazole, oxazole, pyrazole, pyridine, pyridazine, pyrimidine, pyrazine, benzoxazole, benzothiazole, benzothiophene, dibenzothiophene, benzofuran, benzimidazole, indole, indazole, quinoline, isoquinoline, quinoxaline, tetrahydrothiophene, tetrahydrothiopyran, oxirane, tetrahydrofuran, tetrahydropyran, pyrrolidine, piperidine, morpholine, thiomorpholine, piperazine, isoxazole, oxadiazole, thiadiazole, imidazoline, imidazolone, imidazolidone, hydantoin, oxazoline, oxazolone, uracil and triazolone.

In case that the heterocyclic groups have substituents, the following can be their substituents: e.g. a halogen atom, an alkyl group, an alkoxy group, an alkylthio group, an alkylsulfonyl group, a haloalkyl group, haloalkoxy group, a nitro group, a cyano group, an alkylcarbonyl group, a phenyl group, a substituted aryl group.

The compounds which are preferably responsible for the activity of preventing the pests in the present invention are the ones according to the general formula (I), in which R represents a methyl group substituted by a cycloalkyl group having 3 to 8 carbon atoms, an alkyl group having 1 to 4 carbon atoms substituted by a phenyl group which may be substituted or a methyl group substituted by pyridyl group which may be substituted;

R' represents hydrogen atom;

J represents

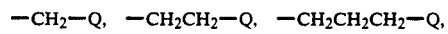

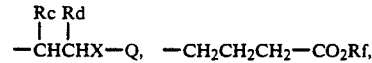

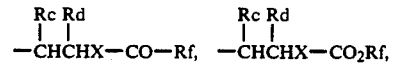

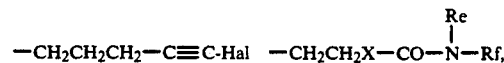

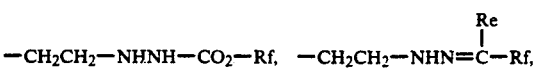

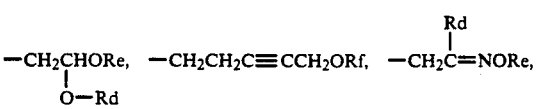

-continued

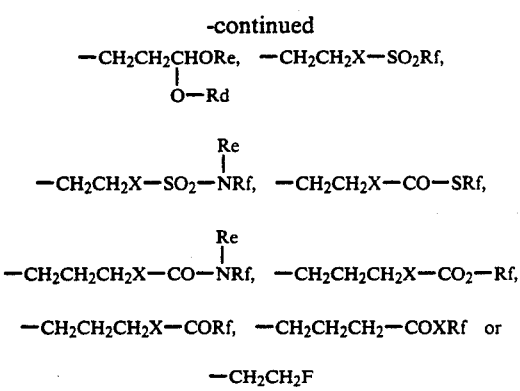

wherein Rc, Rd and Re independently represent a hydrogen atom or an alkyl group having 1 to 4 carbon atoms; Rf represents a hydrogen atom, an alkyl group having 1 to 4 carbon atoms, an alkenyl group having 2 to 8 carbon atoms, a cycloalkyl group having 3 to 8 carbon atoms and a phenyl group which may be substituted;

X represents —O—, —NH— or

(Rg represents an alkyl group having 1 to 4 carbon atoms.), Hal represents a halogen atom, Q represents an phenyl group which may be substituted, or a pyridyl group, a pyrimidyl group, a pyridazyl group, an isoxazol group, an oxadiazolyl group or a thiazolyl group which may be substituted.

As the more preferable compounds, as being exemplified by the compound Nos. of Table 2 mentioned later, such as the following compounds may be mentioned. For example. Compound Nos. 5, 6, 8, 9, 19, 20, 31, 32, 33, 34, 39, 42, 45, 46, 47, 57, 67, 68, 69, 71, 75, 77, 79, 80, 81 and 82.

No. 5
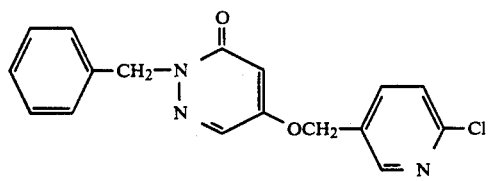

No. 6
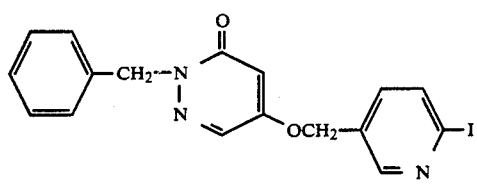

No. 8
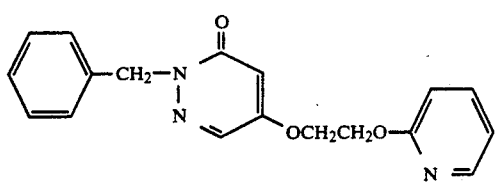

No. 20
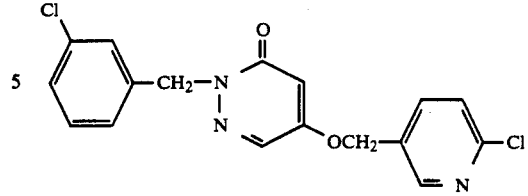

No. 31
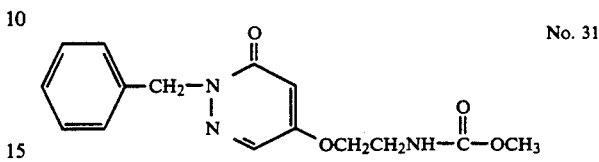

No. 32
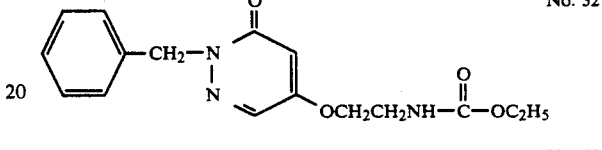

No. 33
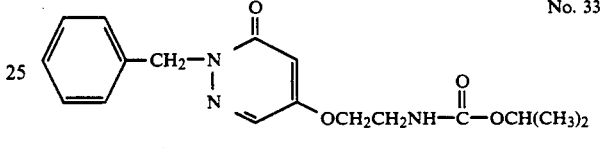

No. 46
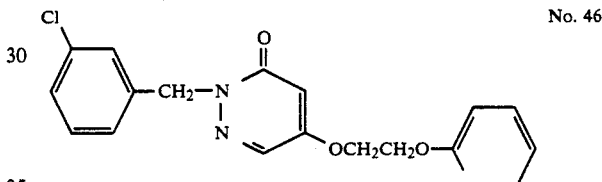

No. 47
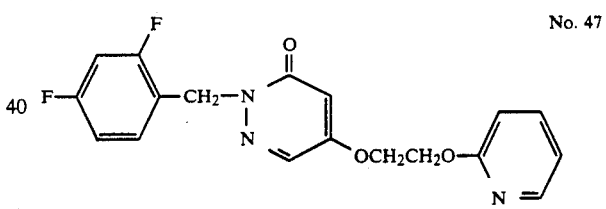

No. 57
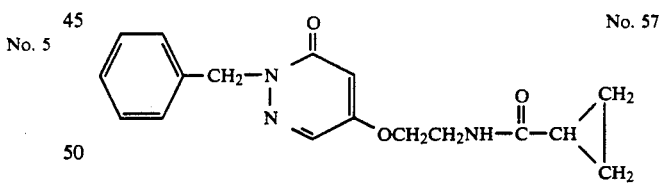

The compounds of the present invention may be produced by many producing methods. The methods are, for example, as follows:

Scheme (1)

Process 1-a

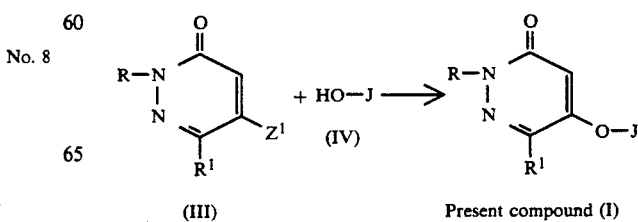

-continued
Scheme (1)

Process 1-b

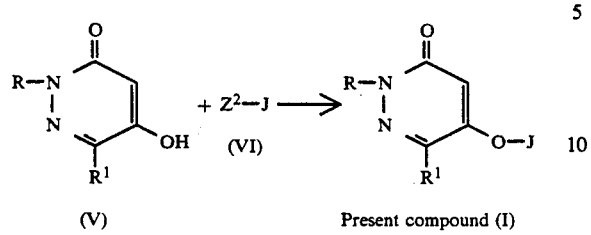

(V)  Present compound (I)

Scheme (2)

Process 2-a

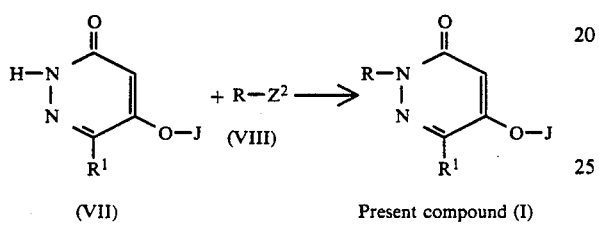

(VII)  Present compound (I)

Process 2-b

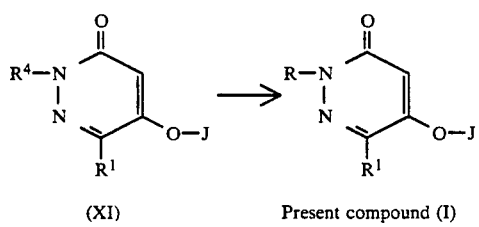

(XI)  Present compound (I)

Scheme (3)

Process 3-a

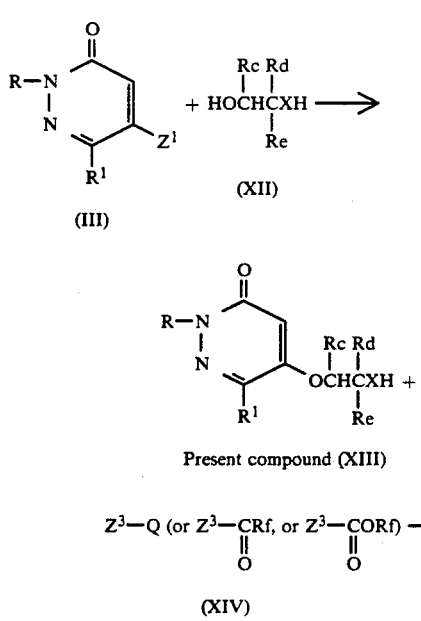

$Z^3$—Q (or $Z^3$—CRf, or $Z^3$—CORf) $\longrightarrow$
          ‖              ‖
          O              O (XIV)

-continued
Scheme (3)

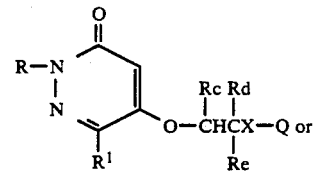

Present compound

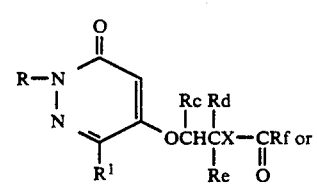

Present compound

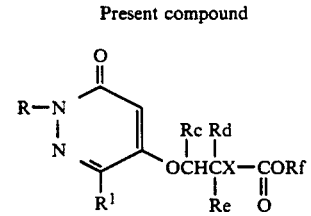

Present compound

Process 3-b

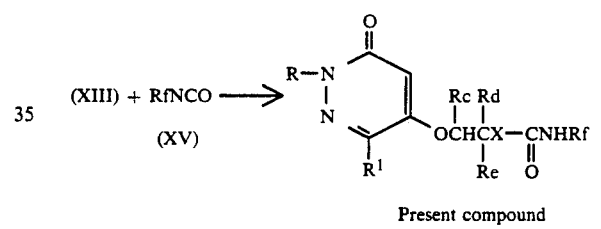

Present compound

In the above schemes (1), (2) and (3), R, R', X, Rc, Rd, Re, Rf, Q and J each have the same meanings as defined above and $Z^1$ represents a halogen, atom or azole group; $Z^2$ represents a halogen atom, an alkylsulfonate group or an arylsulfonate group; $Z^3$ represents a halogen atom, $R^4$ represents substituents having reactive functional group.

In the reaction shown in the schemes (1), (2) and (3), as the a solvent may be used lower alcohols such as methanol, ethanol; ketones such as acetone and methylethylketone; hydrocarbons such as benzene and toluene; ethers such as isopropyl ether, tetrahydrofuran and 1,4-dioxane; amides such as N,N-dimethylformamides and hexamethyl phosphoric triamide; halogenated hydrocarbons such as dichloromethane and dichloroethane. If necessary, these solvents may be used as a mixture or mixture with water.

As a base may be used inorganic bases such as sodium hydride, sodium hydroxide, potassium hydroxide, sodium carbonate, potassium carbonate, sodium hydrogencarbonate and organic bases such as sodium methoxide, sodium ethoxide, triethylamine, pyridine, etc. If necessary, a tetraammonium salt such as triethylbenzylammonium chloride or the like can be added to the reaction system as a catalyst. The reaction temperature ranges from −20° C. to the boiling point of the solvent used in the reaction system, and is preferably in the range of −5° C. to the boiling point of the solvent used therein. Molar ratio of the starting materials can be optionally selected for the reaction. However, it is advantageous to use the materials in an equimolar ratio or near such ratio.

More specifically, in the Process 1-a of the scheme (1), the compound of the present invention of the formula (I) can be produced by reacting Z' of the compound of the formula (III) with alcohols of the formula (IV) in a suitable solvent in the presence of a base. Z' is preferably a halogen atom, especially, chlorine or bromine atom, and azoles, especially, 1-imidazole. As a solvent, it is preferable to use N,N-dimethylformamide, methanol, ethanol, toluene and a mixture solvent of toluene-water. As a base, it is preferable to use inorganic bases, especially sodium carbonate, potassium carbonate, sodium hydroxide and potassium hydroxide. The reaction temperature is preferably in the range of from 20° C. to 50° C.

In the Process 1-b, the present compounds can be produced by reacting pyridazinone derivatives of the formula (V) with alkyl halides or alkylsufonates of the formula (VI) in a suitable solvent in the presence of a base. $Z^2$ is it is preferable to use N,N-dimethylformamide, methanol, ethanol, acetonitrile, 1,2-dichloroethane, toluene and a mixture solvent of toluene-water. As a base, it is preferable to use inorganic bases, especially, sodium carbonate, potassium carbonate, sodium hydroxide and potassium hydroxide. The reaction temperature is preferably in the range of from 20° C. to 120° C. When sodium iodide, potassium iodide, tetrabutylammonium iodide are added in the reaction process, an excellent result may be obtained by the acceleration of the reaction.

In the Process 2-a of the scheme (2), the present compounds can be produced by alkylating the 2-position of pyridazinone derivatives of the formula (VII) with $R-Z^2$ of the formula (VIII). In the above procedure, the present compounds may be readily produced by adding inorganic or organic bases to the reaction system to raise the reactivity of the pyridazinone derivatives of the formula (VII).

The Process 2-b of the scheme (2) is a method to produce the present compound of the formula (I) by chemically modifying the functional groups in the N-substituent ($R^4$) of the pyridazinone derivatives of the formula (XI) to be converted into an intended N-substituent (R).

Concretely, a method in which a halogen atom contained in $R^4$ is dehalogenated is mentioned.

The Process 3-a of the scheme (3) produces compounds of the formula (XIII) by reacting the compound of the formula (III) with the compound of the formula (XII) in a suitable solvent in the presence of the above base. Further, the produced compound is reacted with heterocyclic halides or acid halides of the formula (XIV) in a suitable solvent in the presence of the base to produce the present compounds.

As the solvent to be used, benzene, toluene, tetrahydrofuran, 1,2-dichloroethane and N,N-dimethylformamide etc. are preferable, and as the base, organic bases are preferable, especially triethylamine or pyridine etc. Inorganic bases also may be used. The reaction temperature is preferably in the range of 0° C. to 50° C.

The Process 3-b of the scheme (3) produces compounds of the present invention by reacting the compound of the formula (XIII) of the present invention with an isocyanate compound of the formula (XV) in a suitable solvent.

As a solvent, benzene, toluene, tetrahydrofuran and 1,2-dichloroethane etc. are preferable, and the reaction temperature is preferably in the range of 0° C. to 50° C. If necessary, organic bases such as triethylamine, pyridine or hexamethylenetetramine may be added in the reaction process.

As a method for preparing the compounds of the present invention, the following reactions are also useful.

Process 4-a

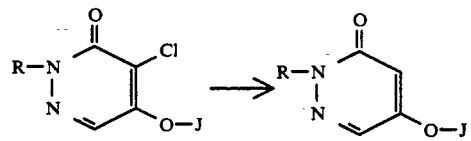

Process 4-b

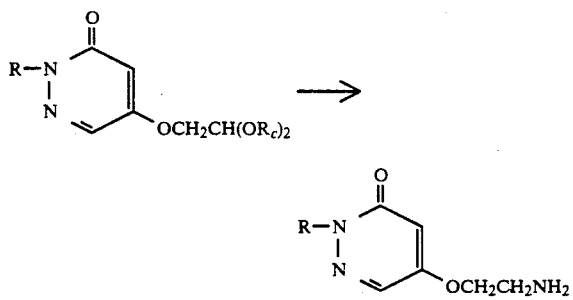

Process 4-c

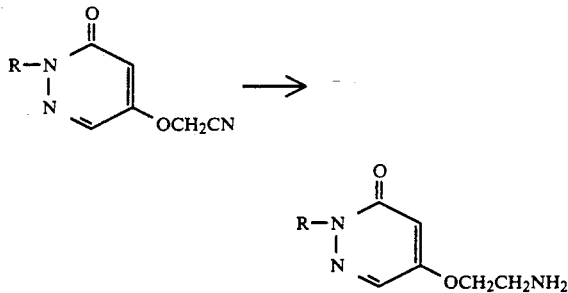

Process 4-d

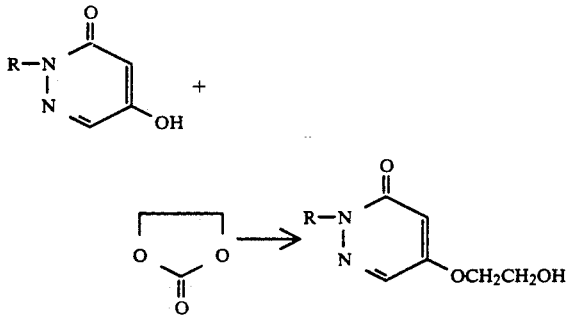

In the Process 4-a and 4-d, R, Rc and J represent the same meanings as described above).

The Process 4-a of the scheme (4), the compound of the present invention can be produced by dehalogenating the chlorine of 4-position of pyridazinone ring in a hydrogenating reaction. The application of this method is limited to the case where R and J are stable to the hydrogenating reaction.

The Processes 4-b and 4-c of the scheme (4) are useful for synthesizing a compound of pyridazinone containing a 2-aminoethyloxy group in the 5-position. The Process 4-b of the scheme (4) is characterized in that the reaction is carried out through an acetal compound, and the Process 4-c is characterized in that the reaction is reducing the nitrile group of the pyridazinone.

The Process 4-d of the scheme (4) is useful for synthesizing a compound of pyridazinone containing 2-hydroxyethyloxy group in the 5-position. The process is characterized in that the corresponding 5-hydroxypyridazinone compound is heated in the presence of an ethylenecarbonate and a base.

The compounds encompassed by the present invention are illustrated in detail by the compounds listed in Table 1. However, it should be understood that the compounds in Table 1 are merely illustrative and not to restrict the present invention.

In the Table, Me represents methyl, Et represents ethyl, Pr represents propyl, Bu represents butyl, Ph represents unsubstituted phenyl, t represents tertiary, s represents secondary, i represents iso.

Incidentally, a compound of the present invention which contains asymmetric carbon atom(s) includes an optically active (+) compound and (−) compound.

Furthermore, compounds among the present invention in which geometric isomers exist therein include cis compound and transcompounds.

TABLE 1

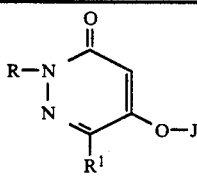

In the compound represented by the general formula (I),

| R | R$^1$ | J |
|---|---|---|
| PhCH$_2$ | H | CH$_2$C$_6$H$_4$(Et)-4 |
| PhCH$_2$ | H | CH$_2$C$_6$H$_4$(Cl)-4 |
| PhCH$_2$ | H | CH$_2$C$_6$H$_4$(I)-4 |
| PhCH$_2$ | H | CH$_2$C$_6$H$_3$(Cl$_2$)-2,4 |
| PhCH$_2$ | H | CH$_2$(Q26-Cl-6) |
| PhCH$_2$ | H | CH$_2$(Q26-I-6) |
| PhCH$_2$ | H | CH$_2$CH$_2$OPh |
| PhCH$_2$ | H | CH$_2$CH$_2$O(Q17) |
| PhCH$_2$ | H | CH$_2$CH(Me)O(Q17) |
| PhCH$_2$ | Cl | CH$_2$CH$_2$O(Q17) |
| PhCH$_2$ | Cl | CH$_2$CH(Me)O(Q17) |
| PhCH$_2$ | Br | CH$_2$CH$_2$O(Q17) |
| PhCH$_2$ | F | CH$_2$CH(Me)O(Q17) |
| PhCH$_2$ | OMe | CH$_2$CH$_2$(Q17) |
| PhCH$_2$ | OEt | CH$_2$CH(Me)O(Q17) |
| PhCH$_2$ | OH | CH$_2$CH$_2$O(Q17) |
| PhCH$_2$ | H | CH$_2$CH=NOPr |
| PhCH$_2$ | H | CH$_2$CH$_2$ON=CHMe |
| PhCH$_2$ | H | CH$_2$CH$_2$Ph |
| PhCH$_2$ | H | CH$_2$CH$_2$CH$_2$Ph |
| PhCH$_2$ | H | CH$_2$CH=CHC$_6$H$_4$(Et)-4 |
| PhCH$_2$ | H | CH$_2$(Q17-Me-5) |
| PhCH$_2$ | H | CH$_2$(Q18) |
| PhCH$_2$ | H | CH$_2$(Q22-Cl-5) |
| PhCH$_2$ | H | CH$_2$(Q23-Cl-5) |
| PhCH$_2$ | H | CH$_2$(Q27-Cl-6) |
| PhCH$_2$ | H | CH$_2$(Q28-Cl-4) |
| PhCH$_2$ | H | CH$_2$(Q27-Me-4) |
| PhCH$_2$ | H | CH$_2$(Q32-Me-2) |
| PhCH$_2$ | H | CH$_2$(Q45-Cl-5) |
| PhCH$_2$ | H | CH$_2$(Q50-Cl-2) |
| PhCH$_2$ | H | CH$_2$CH$_2$CH$_2$CO$_2$Et |

TABLE 1-continued

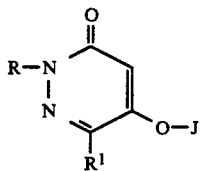

In the compound represented by the general formula (I),

| R | R$^1$ | J |
|---|---|---|
| PhCH$_2$ | H | CH$_2$CH=CHCOOMe |
| PhCH$_2$ | H | CH$_2$CH$_2$OCOMe |
| PhCH$_2$ | H | CH$_2$CH$_2$OCOPh |
| PhCH$_2$ | H | CH$_2$CH$_2$NHCOEt |
| PhCH$_2$ | H | CH$_2$CH$_2$NHCOPh |
| PhCH$_2$ | H | CH$_2$CH$_2$NHCO$_2$Me |
| PhCH$_2$ | H | CH$_2$CH$_2$NHCONMe$_2$ |
| PhCH$_2$ | H | CH$_2$CH$_2$CH$_2$C≡CMe |
| PhCH$_2$ | H | CH$_2$CO$_2$Me |
| PhCH$_2$ | H | CH$_2$CO$_2$Bu |
| PhCH$_2$ | H | CH$_2$CO$_2$Ph |
| PhCH$_2$ | H | CH$_2$CONH$_2$ |
| PhCH$_2$ | H | CH$_2$CONMe$_2$ |
| PhCH$_2$ | H | CH$_2$CONHPh |
| PhCH$_2$ | H | CH$_2$CH$_2$NHNHCO$_2$Me |
| PhCH$_2$ | H | CH$_2$CH$_2$NHN=CMe$_2$ |
| PhCH$_2$ | H | CH$_2$CH$_2$C≡CCH$_2$OMe |
| PhCH$_2$ | H | CH$_2$C(Me)=NOPr |
| PhCH$_2$ | H | CH$_2$CH(OEt)$_2$ |
| (4-ClC$_6$H$_4$)CH$_2$ | H | CH$_2$C$_6$H$_4$(Et)-4 |
| (3,4-Cl$_2$C$_6$H$_3$)CH$_2$ | H | CH$_2$C$_6$H$_4$(Cl)-4 |
| PhCH$_2$CH$_2$ | H | CH$_2$(Q26-Cl-6) |
| Ph$_2$CH | H | CH$_2$(Q26-I-6) |
| PhCH$_2$CH$_2$CH$_2$ | H | CH$_2$C$_6$H$_4$(CF$_3$)-4 |
| PhCH$_2$CH(Ph)CH$_2$ | H | CH$_2$(Q26-Cl-6) |
| (Q1)CH$_2$ | H | CH$_2$CH(Me)O(Q17) |
| (Q2)CH$_2$ | H | CH$_2$(Q26-Cl-6) |
| (Q3)CH$_2$ | H | CH$_2$C$_6$H$_4$(Et)-4 |
| (Q4)CH$_2$ | H | CH$_2$C$_6$H$_4$(I)-4 |
| (Q4)CH$_2$ | H | CH$_2$(Q26-Cl-6) |
| (Q4)CH$_2$ | H | CH$_2$(Q26-I-6) |
| (Q4)CH$_2$ | H | CH$_2$CH$_2$OPh |
| (Q4)CH$_2$ | H | CH$_2$CH(Me)OPh |
| (Q4)CH$_2$ | H | CH$_2$CH$_2$O(Q17) |
| (Q4)CH$_2$ | H | CH$_2$CH(Me)O(Q17) |
| (Q4)CH$_2$ | Cl | CH$_2$CH(Me)O(Q17) |
| (Q4)CH$_2$ | H | CH$_2$C(Me)=NOPr |
| (Q4)CH$_2$ | H | CH$_2$CH$_2$NHCOOEt |
| (Q4)CH$_2$ | H | CH$_2$CH$_2$CH$_2$C≡CCl |
| (Q5)CH$_2$ | H | CH$_2$CH(Me)O(Q17) |
| (Q6)CH$_2$ | H | CH$_2$(Q26-Cl-6) |
| (Q7)CH$_2$ | H | CH$_2$C$_6$H$_4$(Et)-4 |
| (Q8)CH$_2$ | H | CH$_2$C$_6$H$_4$(I)-4 |
| (Q9)CH$_2$ | H | CH$_2$(Q26-Cl-6) |
| (Q10)CH$_2$ | H | CH$_2$(Q26-I-6) |
| (Q11)CH$_2$ | H | CH$_2$CH(Me)OPh |
| (Q12)CH$_2$ | H | CH$_2$CH$_2$O(Q17) |
| (Q13)CH$_2$ | H | CH$_2$CH(Me)O(Q17) |
| (Q14)CH$_2$ | H | CH$_2$C$_6$H$_4$(Et)-4 |
| (Q15)CH$_2$ | H | CH$_2$C$_6$H$_4$(CF$_3$)-4 |
| (Q16)CH$_2$ | H | CH$_2$C$_6$H$_4$(Cl)-4 |
| (Q17)CH$_2$ | H | CH$_2$CH(Me)O(Q17) |
| (Q18)CH$_2$ | H | CH$_2$C$_6$H$_4$(CF$_3$)-4 |
| (Q22)CH$_2$ | H | CH$_2$(Q26-Cl-6) |
| (Q23)CH$_2$ | H | CH$_2$(Q26-I-6) |
| (Q26)CH$_2$ | H | CH$_2$C$_6$H$_4$(Et)-4 |
| (Q27-Cl-6)CH$_2$ | H | CH$_2$C$_6$H$_4$(Cl)-4 |
| (Q28)CH$_2$ | H | CH$_2$CH$_2$O(Q17) |
| (Q30)CH$_2$ | H | CH$_2$(Q26-Cl-6) |
| (Q31)CH$_2$ | H | CH$_2$CH(Me)O(Q17) |
| (Q32)CH$_2$ | H | CH$_2$CH$_2$O(Q17) |
| (Q33)CH$_2$ | H | CH$_2$C$_6$H$_4$(CF$_3$)-4 |
| (Q45)CH$_2$ | H | CH$_2$(Q26-Cl-6) |
| (Q46)CH$_2$ | H | CH$_2$(Q26-I-6) |
| 3-MeC$_6$H$_4$CH$_2$ | H | CH$_2$(Q26-Cl-6) |
| 3-ClC$_6$H$_4$CH$_2$ | H | CH$_2$(Q26-Cl-6) |
| 2,4-F$_2$C$_6$H$_3$CH$_2$ | H | CH$_2$(Q26-I-6) |
| PhCH$_2$ | H | CH$_2$CO$_2$H |
| PhCH$_2$ | H | CH$_2$CO$_2$Et |
| PhCH$_2$ | H | CH$_2$CO$_2$Pr-i |

TABLE 1-continued

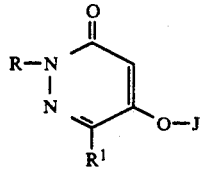

In the compound represented by the general formula (I),

| R | R¹ | J |
|---|----|---|
| PhCH$_2$ | H | CH$_2$CO$_2$Bu-t |
| PhCH$_2$ | H | CH$_2$CONHEt |
| PhCH$_2$ | H | CH$_2$CONHPr |
| PhCH$_2$ | H | CH$_2$CONHBu |
| PhCH$_2$ | H | CH$_2$CH$_2$NH$_2$ |
| PhCH$_2$ | H | CH$_2$CH$_2$NHCO$_2$Et |
| PhCH$_2$ | H | CH$_2$CH$_2$NHCO$_2$Pr |
| PhCH$_2$ | H | CH$_2$CH$_2$NHCO$_2$Pr-i |
| 2,4-F$_2$C$_6$H$_3$CH$_2$ | H | CH$_2$CH$_2$NHCO$_2$Et |
| PhCH$_2$ | H | CH$_2$CH$_2$NHCO$_2$Ph |
| PhCH$_2$ | H | CH$_2$CH$_2$NHCOPr |
| PhCH$_2$ | H | CH$_2$CH$_2$NHCONHEt |
| PhCH$_2$ | H | CH$_2$CH$_2$OH |
| PhCH$_2$ | H | CH$_2$CH$_2$OCONHEt |
| PhCH$_2$ | H | CH$_2$CH$_2$OCONHPr-i |
| PhCH$_2$ | H | CH$_2$CH$_2$OCONHPh |
| 3-MeC$_6$H$_4$CH$_2$ | H | CH$_2$CH$_2$O(Q17) |
| 3-ClC$_6$H$_4$CH$_2$ | H | CH$_2$CH$_2$O(Q17) |
| 2,4-F$_2$C$_6$H$_3$CH$_2$ | H | CH$_2$CH$_2$O(Q17) |
| PhCH$_2$ | H | CH$_2$CH$_2$O(Q27) |
| PhCH$_2$ | H | CH$_2$CH$_2$OBu-i |
| PhCH$_2$ | H | CH$_2$CH$_2$CH(OEt)$_2$ |
| PhCH$_2$ | H | CH$_2$CH$_2$NHSO$_2$Et |
| PhCH$_2$ | H | CH$_2$CH$_2$NHSO$_2$NMe$_2$ |
| PhCH$_2$ | H | CH$_2$CH$_2$NHC(O)SEt |
| PhCH$_2$ | H | CH$_2$CH$_2$NHCOC(Me)=CH$_2$ |
| PhCH$_2$ | H | CH$_2$CH$_2$NHCOCH=C(Me)$_2$ |
| PhCH$_2$ | H | CH$_2$CH$_2$NHCO(Q1) |
| PhCH$_2$ | H | (CH$_2$)$_3$OCONHEt |
| PhCH$_2$ | H | (CH$_2$)$_3$NHCO$_2$Et |
| PhCH$_2$ | H | (CH$_2$)$_3$NHCO$_2$Me |
| PhCH$_2$ | H | CH$_2$CH$_2$OCO(Q1) |
| PhCH$_2$ | H | (CH$_2$)$_3$OCO(Q1) |
| 3-CF$_3$C$_6$H$_4$CH$_2$ | H | CH$_2$CH$_2$O(Q17) |
| 3-CF$_3$C$_6$H$_4$CH$_2$ | H | CH$_2$(Q26-Cl-6) |
| 3,5-Cl$_2$C$_6$H$_3$CH$_2$ | H | CH$_2$CH$_2$O(Q17) |
| 3,5-Cl$_2$C$_6$H$_3$CH$_2$ | H | CH$_2$(Q26-I-6) |
| 3-CF$_3$C$_6$H$_4$CH$_2$ | H | CH$_2$CH$_2$NHCO$_2$Me |
| 3-CF$_3$C$_6$H$_4$CH$_2$ | H | CH$_2$CH$_2$NHCO$_2$Et |
| 3-CF$_3$C$_6$H$_4$CH$_2$ | H | CH$_2$CH$_2$NHCO(Q1) |
| PhCH$_2$ | H | (CH$_2$)$_3$NHCO(Q1) |
| 3,5-Cl$_2$C$_6$H$_3$CH$_2$ | H | CH$_2$CH$_2$NHCO$_2$Et |
| PhCH$_2$ | H | CH$_2$CH(Me)NHCO$_2$Et |
| PhCH$_2$ | H | CH(Me)CH$_2$NHCO(Q1) |
| 3-BrC$_6$H$_4$CH$_2$ | H | CH$_2$(Q26-Cl-6) |
| 3-BrC$_6$H$_4$CH$_2$ | H | CH$_2$CH$_2$O(Q17) |
| 3-BrC$_6$H$_4$CH$_2$ | H | CH$_2$CH$_2$NHCO$_2$Et |
| 3-BrC$_6$H$_4$CH$_2$ | H | CH$_2$(Q26-I-6) |
| 3-BrC$_6$H$_4$CH$_2$ | H | CH$_2$CH$_2$NHCO(Q1) |
| 3-FC$_6$H$_4$CH$_2$ | H | CH$_2$(Q26-I-6) |
| 3-FC$_6$H$_4$CH$_2$ | H | CH$_2$CH$_2$NHCO$_2$Et |
| 3-FC$_6$H$_4$CH$_2$ | H | CH$_2$CH$_2$NHCO(Q1) |
| 3-FC$_6$H$_4$CH$_2$ | H | CH$_2$CH$_2$O(Q17) |
| 4-ClC$_6$H$_4$CH$_2$ | H | CH$_2$(Q26-I-6) |
| 4-ClC$_6$H$_4$CH$_2$ | H | CH$_2$CH$_2$NHCO$_2$Et |
| 4-ClC$_6$H$_4$CH$_2$ | H | CH$_2$CH$_2$NHCO(Q1) |
| 4-ClC$_6$H$_4$CH$_2$ | H | CH$_2$CH$_2$O(Q17) |
| 2-ClC$_6$H$_4$CH$_2$ | H | CH$_2$(Q26-Cl-6) |
| 2-ClC$_6$H$_4$CH$_2$ | H | CH$_2$CH$_2$NHCO$_2$Et |
| 2-ClC$_6$H$_4$CH$_2$ | H | CH$_2$CH$_2$NHCO(Q1) |
| 3-NO$_2$C$_6$H$_4$CH$_2$ | H | CH$_2$(Q26-Cl-6) |
| 3-NO$_2$C$_6$H$_4$CH$_2$ | H | CH$_2$CH$_2$NHCO$_2$Et |
| 3-NO$_2$C$_6$H$_4$CH$_2$ | H | CH$_2$CH$_2$NHCO(Q1) |
| (Q17)CH$_2$ | H | CH$_2$(Q26-Cl-6) |
| (Q17)CH$_2$ | H | CH$_2$CH$_2$NHCO$_2$Et |
| (Q17)CH$_2$ | H | CH$_2$CH$_2$NHCO$_2$Me |
| (Q17)CH$_2$ | H | CH$_2$CH$_2$NHCO(Q1) |
| (Q17)CH$_2$ | H | CH$_2$CH$_2$O(Q17) |
| (Q26)CH$_2$ | H | CH$_2$CH$_2$O(Q17) |
| (Q26)CH$_2$ | H | CH$_2$CH$_2$NHCO$_2$Et |

TABLE 1-continued

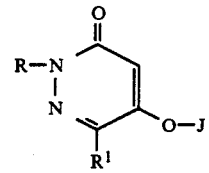

In the compound represented by the general formula (I),

| R | R¹ | J |
|---|----|---|
| (Q26)CH$_2$ | H | CH$_2$CH$_2$NHCO(Q1) |
| (Q26-Cl-6)CH$_2$ | H | CH$_2$CH$_2$NHCO$_2$Et |
| (Q26-Cl-6)CH$_2$ | H | CH$_2$CH$_2$NHCO(Q1) |
| (Q17-CF$_3$-5)CH$_2$ | H | CH$_2$CH$_2$NHCO$_2$Et |
| (Q17-CF$_3$-5)CH$_2$ | H | CH$_2$CH$_2$NHCO(Q1) |
| (Q18)CH$_2$ | H | CH$_2$(Q26-Cl-6) |
| (Q18)CH$_2$ | H | CH$_2$CH$_2$O(Q17) |
| (Q18)CH$_2$ | H | CH$_2$CH$_2$NHCO$_2$Et |
| (Q18)CH$_2$ | H | CH$_2$CH$_2$NHCO(Q1) |
| PhCH$_2$ | H | CH$_2$(Q17-CF$_3$-5) |
| 3-ClC$_6$H$_4$CH$_2$ | H | CH$_2$(Q17-CF$_3$-5) |
| PhCH(Me) | H | CH$_2$(Q26-Cl-6) |
| PhCH(Me) | H | CH$_2$CH$_2$O(Q17) |
| PhCH(Me) | H | CH$_2$CH$_2$NHCO$_2$Et |
| PhCH(Me) | H | CH$_2$CH$_2$NHCO(Q1) |
| PhCH$_2$CH$_2$ | H | CH$_2$(Q26-I-6) |
| PhCH$_2$CH$_2$ | H | CH$_2$CH$_2$O(Q17) |
| PhCH$_2$CH$_2$ | H | CH$_2$CH$_2$NHCO$_2$Et |
| PhCH$_2$CH$_2$ | H | CH$_2$CH$_2$NHCO(Q1) |
| PhCH$_2$ | H | CH$_2$(Q67-Me-3) |
| PhCH$_2$ | H | CH$_2$(Q67-Br-3) |
| PhCH$_2$ | H | CH$_2$[Q67-(Q1)-3] |
| 3-ClC$_6$H$_4$CH$_2$ | H | CH$_2$(Q67-Me-3) |
| 3-ClC$_6$H$_4$CH$_2$ | H | CH$_2$(Q67-Br-3) |
| 3-ClC$_6$H$_4$CH$_2$ | H | CH$_2$[Q67-(Q1)-3] |
| 3-FC$_6$H$_4$CH$_2$ | H | CH$_2$(Q67-Me-3) |
| 3-FC$_6$H$_4$CH$_2$ | H | CH$_2$(Q67-Br-3) |
| 3-BrC$_6$H$_4$CH$_2$ | H | CH$_2$(Q67-Me-3) |
| 3-BrC$_6$H$_4$CH$_2$ | H | CH$_2$(Q67-Br-3) |
| 3-CF$_3$C$_6$H$_4$CH$_2$ | H | CH$_2$(Q67-Me-3) |
| 3-CF$_3$C$_6$H$_4$CH$_2$ | H | CH$_2$(Q67-Br-3) |
| 3,5-Cl$_2$C$_6$H$_3$CH$_2$ | H | CH$_2$(Q67-Me-3) |
| 3,5-Cl$_2$C$_6$H$_3$CH$_2$ | H | CH$_2$(Q67-Br-3) |
| 3,5-Cl$_2$C$_6$H$_3$CH$_2$ | H | CH$_2$[Q67-(Q1)-3] |
| PhCH$_2$ | H | CH$_2$(Q67-Cl-3) |
| 3-ClC$_6$H$_4$CH$_2$ | H | CH$_2$(Q67-Cl-3) |
| 3-FC$_6$H$_4$CH$_2$ | H | CH$_2$(Q67-Cl-3) |
| 3-BrC$_6$H$_4$CH$_2$ | H | CH$_2$(Q67-Cl-3) |
| 3-CF$_3$C$_6$H$_4$CH$_2$ | H | CH$_2$(Q67-Cl-3) |
| 3,5-Cl$_2$C$_6$H$_3$CH$_2$ | H | CH$_2$(Q67-Cl-3) |
| PhCH$_2$ | H | CH$_2$(Q67-I-3) |
| 3-ClC$_6$H$_4$CH$_2$ | H | CH$_2$(Q67-I-3) |
| 3-FC$_6$H$_4$CH$_2$ | H | CH$_2$(Q67-I-3) |
| 3-BrC$_6$H$_4$CH$_2$ | H | CH$_2$(Q67-I-3) |
| 3-CF$_3$C$_6$H$_4$CH$_2$ | H | CH$_2$(Q67-I-3) |
| 3,5-Cl$_2$C$_6$H$_3$CH$_2$ | H | CH$_2$(Q67-I-3) |
| 3-BrC$_6$H$_4$CH$_2$ | H | CH$_2$[Q67-(Q1)-3] |
| 3-CF$_3$C$_6$H$_4$CH$_2$ | H | CH$_2$[Q67-(Q1)-3] |
| PhCH$_2$ | Cl | CH$_2$(Q26-Cl-6) |
| PhCH$_2$ | Br | CH$_2$(Q26-Cl-6) |
| PhCH$_2$ | F | CH$_2$(Q26-Cl-6) |
| PhCH$_2$ | OMe | CH$_2$(Q26-Cl-6) |
| PhCH$_2$ | OH | CH$_2$(Q26-Cl-6) |
| PhCH$_2$ | Cl | CH$_2$(Q26-I-6) |
| PhCH$_2$ | Br | CH$_2$(Q26-I-6) |
| PhCH$_2$ | F | CH$_2$(Q26-I-6) |
| PhCH$_2$ | OMe | CH$_2$(Q26-I-6) |
| PhCH$_2$ | OEt | CH$_2$(Q26-I-6) |
| PhCH$_2$ | F | CH$_2$CH$_2$O(Q17) |
| PhCH$_2$ | OEt | CH$_2$CH$_2$O(Q17) |
| PhCH$_2$ | Cl | CH$_2$CH$_2$NHCO$_2$Et |
| PhCH$_2$ | Br | CH$_2$CH$_2$NHCO$_2$Et |
| PhCH$_2$ | F | CH$_2$CH$_2$NHCO$_2$Et |
| PhCH$_2$ | OMe | CH$_2$CH$_2$NHCO$_2$Et |
| PhCH$_2$ | OEt | CH$_2$CH$_2$NHCO$_2$Et |
| PhCH$_2$ | OH | CH$_2$CH$_2$NHCO$_2$Et |
| PhCH$_2$ | Cl | CH$_2$CH$_2$NHCO$_2$Me |
| PhCH$_2$ | Br | CH$_2$CH$_2$NHCO$_2$Me |
| PhCH$_2$ | OMe | CH$_2$CH$_2$NHCO$_2$Me |
| PhCH$_2$ | Cl | CH$_2$CH$_2$NHCO$_2$Pr-i |

TABLE 1-continued

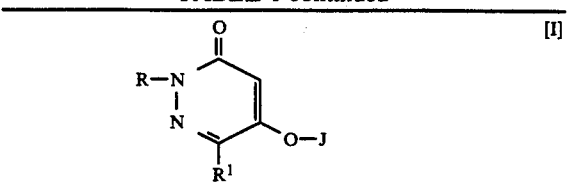

In the compound represented by the general formula (I),

| R | R¹ | J |
|---|---|---|
| PhCH₂ | Br | CH₂CH₂NHCO₂Pr-i |
| PhCH₂ | OMe | CH₂CH₂NHCO₂Pr-i |
| PhCH₂ | Cl | CH₂CH₂NHCO(Q1) |
| PhCH₂ | Br | CH₂CH₂NHCO(Q1) |
| PhCH₂ | F | CH₂CH₂NHCO(Q1) |
| PhCH₂ | OMe | CH₂CH₂NHCO(Q1) |
| 3-ClC₆H₄CH₂ | Cl | CH₂(Q26-Cl-6) |
| 3-ClC₆H₄CH₂ | Br | CH₂(Q26-Cl-6) |
| 3-ClC₆H₄CH₂ | OMe | CH₂(Q26-Cl-6) |
| 3-ClC₆H₄CH₂ | Cl | CH₂CH₂O(Q17) |
| 3-ClC₆H₄CH₂ | Br | CH₂CH₂O(Q17) |
| 3-ClC₆H₄CH₂ | OMe | CH₂CH₂O(Q17) |
| 2,4-F₂C₆H₃CH₂ | Cl | CH₂CH₂O(Q17) |
| 2,4-F₂C₆H₃CH₂ | Br | CH₂CH₂O(Q17) |
| 2,4-F₂C₆H₃CH₂ | F | CH₂CH₂O(Q17) |
| 2,4-F₂C₆H₃CH₂ | OMe | CH₂CH₂O(Q17) |
| PhCH₂ | H | CH(Me)CH₂NHCO(Q1) |
| 3-ClC₆H₄CH₂ | H | CH(Me)CH₂NHCO(Q1) |
| 3-FC₆H₄CH₂ | H | CH(Me)CH₂NHCO(Q1) |
| 3-CF₃C₆H₄CH₂ | H | CH(Me)CH₂NHCO(Q1) |
| 3-BrC₆H₄CH₂ | H | CH(Me)CH₂NHCO(Q1) |
| 2,4-F₂C₆H₃CH₂ | H | CH(Me)CH₂NHCO(Q1) |
| 3,5-Cl₂C₆H₃CH₂ | H | CH(Me)CH₂NHCO(Q1) |
| PhCH₂ | H | CH₂CH₂NHCO(Q1-Me-2) |
| 3-ClC₆H₄CH₂ | H | CH₂CH₂NHCO(Q1-Me-2) |
| 3-FC₆H₄CH₂ | H | CH₂CH₂NHCO(Q1-Me-2) |
| 3-CF₃C₆H₄CH₂ | H | CH₂CH₂NHCO(Q1-Me-2) |
| 3-BrC₆H₄CH₂ | H | CH₂CH₂NHCO(Q1-Me-2) |
| 2,4-F₂C₆H₃CH₂ | H | CH₂CH₂NHCO(Q1-Me-2) |
| 3,5-Cl₂C₆H₃CH₂ | H | CH₂CH₂NHCO(Q1-Me-2) |
| PhCH₂ | H | CH₂CH₂O(Q28) |
| 3-ClC₆H₄CH₂ | H | CH₂CH₂O(Q28) |
| 3-FC₆H₄CH₂ | H | CH₂CH₂O(Q28) |
| 3-CF₃C₆H₄CH₂ | H | CH₂CH₂O(Q28) |
| 3-BrC₆H₄CH₂ | H | CH₂CH₂O(Q28) |
| 2,4-F₂C₆H₃CH₂ | H | CH₂CH₂O(Q28) |
| 3,5-Cl₂C₆H₃CH₂ | H | CH₂CH₂O(Q28) |
| PhCH₂ | H | CH₂[Q68-(Q1)-5] |
| 3-ClC₆H₄CH₂ | H | CH₂[Q68-(Q1)-5] |
| 3-FC₆H₄CH₂ | H | CH₂[Q68-(Q1)-5] |
| 3-CF₃C₆H₄CH₂ | H | CH₂[Q68-(Q1)-5] |
| 3-BrC₆H₄CH₂ | H | CH₂[Q68-(Q1)-5] |
| 2,4-F₂C₆H₃CH₂ | H | CH₂[Q68-(Q1)-5] |
| 3,5-Cl₂C₆H₃CH₂ | H | CH₂[Q68-(Q1)-5] |
| PhCH₂ | H | CH₂(Q69-OEt-5) |
| 3-ClC₆H₄CH₂ | H | CH₂(Q69-OEt-5) |
| 3-FC₆H₄CH₂ | H | CH₂(Q69-OEt-5) |
| 3-CF₃C₆H₄CH₂ | H | CH₂(Q69-OEt-5) |
| 3-BrC₆H₄CH₂ | H | CH₂(Q69-OEt-5) |
| 2,4-F₂C₆H₃CH₂ | H | CH₂(Q69-OEt-5) |
| 3,5-Cl₂C₆H₃CH₂ | H | CH₂(Q69-OEt-5) |
| PhCH₂ | H | CH₂(Q70-Cl₂-4,5) |
| 3-ClC₆H₄CH₂ | H | CH₂(Q70-Cl₂-4,5) |
| 3-FC₆H₄CH₂ | H | CH₂(Q70-Cl₂-4,5) |
| 3-CF₃C₆H₄CH₂ | H | CH₂(Q70-Cl₂-4,5) |
| 3-BrC₆H₄CH₂ | H | CH₂(Q70-Cl₂-4,5) |
| 2,4-F₂C₆H₃CH₂ | H | CH₂(Q70-Cl₂-4,5) |
| 3,5-Cl₂C₆H₃CH₂ | H | CH₂(Q70-Cl₂-4,5) |
| PhCH₂ | H | (CH₂)₃C≡C—Cl |
| 3-ClC₆H₄CH₂ | H | (CH₂)₃C≡C—Cl |
| 3-FC₆H₄CH₂ | H | (CH₂)₃C≡C—Cl |
| 3-CF₃C₆H₄CH₂ | H | (CH₂)₃C≡C—Cl |
| 3-BrC₆H₄CH₂ | H | (CH₂)₃C≡C-Cl |
| 2,4-F₂C₆H₃CH₂ | H | (CH₂)₃C≡C-Cl |
| 3,5-Cl₂C₆H₃CH₂ | H | (CH₂)₃C≡C-Cl |
| 4-FC₆H₄CH₂ | H | CH₂(Q26-Cl-6) |
| 4-FC₆H₄CH₂ | H | CH₂CH₂NHCO₂Et |
| 4-FC₆H₄CH₂ | H | CH₂CH₂NHCO(Q1) |
| 4-FC₆H₄CH₂ | H | CH₂CH₂O(Q17) |
| 2-FC₆H₄CH₂ | H | CH₂(Q26-Cl-6) |
| 2-FC₆H₄CH₂ | H | CH₂CH₂NHCO₂Et |
| 2-FC₆H₄CH₂ | H | CH₂CH₂NHCO(Q1) |
| 2-FC₆H₄CH₂ | H | CH₂CH₂O(Q17) |
| 2,4-Cl₂C₆H₃CH₂ | H | CH₂(26-Cl-6) |
| 2,4-Cl₂C₆H₃CH₂ | H | CH₂CH₂NHCO₂Et |
| 2,4-Cl₂C₆H₃CH₂ | H | CH₂CH₂NHCO(Q1) |
| 2,4-Cl₂C₆H₃CH₂ | H | CH₂CH₂O(Q17) |
| (Q1)CH₂ | H | CH₂CH₂NHCO₂Et |
| (Q2)CH₂ | H | CH₂CH₂NHCO₂Et |
| (Q3)CH₂ | H | CH₂CH₂NHCO₂Et |
| (Q5)CH₂ | H | CH₂CH₂NHCO₂Et |
| (Q6)CH₂ | H | CH₂CH₂NHCO₂Et |
| (Q7)CH₂ | H | CH₂CH₂NHCO₂Et |
| (Q8)CH₂ | H | CH₂CH₂NHCO₂Et |
| (Q9)CH₂ | H | CH₂CH₂NHCO₂Et |
| (Q10)CH₂ | H | CH₂CH₂NHCO₂Et |
| (Q11)CH₂ | H | CH₂CH₂NHCO₂Et |
| (Q12)CH₂ | H | CH₂CH₂NHCO₂Et |
| (Q13)CH₂ | H | CH₂CH₂NHCO₂Et |
| (Q14)CH₂ | H | CH₂CH₂NHCO₂Et |
| (Q15)CH₂ | H | CH₂CH₂NHCO₂Et |
| (Q16)CH₂ | H | CH₂CH₂NHCO₂Et |
| (Q22)CH₂ | H | CH₂CH₂NHCO₂Et |
| (Q23)CH₂ | H | CH₂CH₂NHCO₂Et |
| (Q27)CH₂ | H | CH₂CH₂NHCO₂Et |
| (Q27-Cl-6)CH₂ | H | CH₂CH₂NHCO₂Et |
| (Q28)CH₂ | H | CH₂CH₂NHCO₂Et |
| (Q30)CH₂ | H | CH₂CH₂NHCO₂Et |
| (Q31)CH₂ | H | CH₂CH₂NHCO₂Et |
| (Q32)CH₂ | H | CH₂CH₂NHCO₂Et |
| (Q33)CH₂ | H | CH₂CH₂NHCO₂Et |
| (Q45)CH₂ | H | CH₂CH₂NHCO₂Et |
| (Q46)CH₂ | H | CH₂CH₂NHCO₂Et |
| (Q1)CH₂ | H | CH₂CH₂NHCO(Q1) |
| (Q2)CH₂ | H | CH₂CH₂NHCO(Q1) |
| (Q3)CH₂ | H | CH₂CH₂NHCO(Q1) |
| (Q4)CH₂ | H | CH₂CH₂NHCO(Q1) |
| (Q5)CH₂ | H | CH₂CH₂NHCO(Q1) |
| (Q6)CH₂ | H | CH₂CH₂NHCO(Q1) |
| (Q7)CH₂ | H | CH₂CH₂NHCO(Q1) |
| (Q8)CH₂ | H | CH₂CH₂NHCO(Q1) |
| (Q9)CH₂ | H | CH₂CH₂NHCO(Q1) |
| (Q10)CH₂ | H | CH₂CH₂NHCO(Q1) |
| (Q11)CH₂ | H | CH₂CH₂NHCO(Q1) |
| (Q12)CH₂ | H | CH₂CH₂NHCO(Q1) |
| (Q13)CH₂ | H | CH₂CH₂NHCO(Q1) |
| (Q14)CH₂ | H | CH₂CH₂NHCO(Q1) |
| (Q15)CH₂ | H | CH₂CH₂NHCO(Q1) |
| (Q16)CH₂ | H | CH₂CH₂NHCO(Q1) |
| (Q22)CH₂ | H | CH₂CH₂NHCO(Q1) |
| (Q23)CH₂ | H | CH₂CH₂NHCO(Q1) |
| (Q27)CH₂ | H | CH₂CH₂NHCO(Q1) |
| (Q27-Cl-6)CH₂ | H | CH₂CH₂NHCO(Q1) |
| (Q28)CH₂ | H | CH₂CH₂NHCO(Q1) |
| (Q30)CH₂ | H | CH₂CH₂NHCO(Q1) |
| (Q31)CH₂ | H | CH₂CH₂NHCO(Q1) |
| (Q32)CH₂ | H | CH₂CH₂NHCO(Q1) |
| (Q33)CH₂ | H | CH₂CH₂NHCO(Q1) |
| (Q45)CH₂ | H | CH₂CH₂NHCO(Q1) |
| (Q46)CH₂ | H | CH₂CH₂NHCO(Q1) |
| PhCH₂ | H | CH₂CH₂F |
| 3-FC₆H₄CH₂ | H | CH₂CH₂F |
| PhCH₂ | H | CHF₂ |
| PhCH₂ | H | CF₂Br |
| PhCH₂ | H | CF₂CHF₂ |
| PhCH₂ | H | CF₂CHFCF₃ |

Q1 to Q70 in Table 1 are the groups represented

-continued
by the following formulae.
| | | |
|---|---|---|
| Q1  | Q15 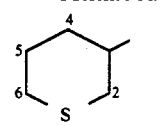 | |
| Q2  | Q16 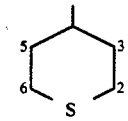 | |
| Q3  | Q17 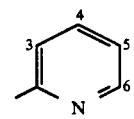 | |
| Q4 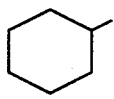 | Q18 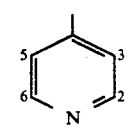 | |
| Q5 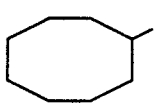 | Q19 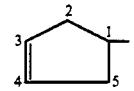 | |
| Q6 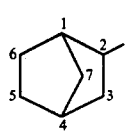 | Q20  | |
| Q7 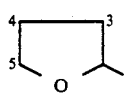 | Q21 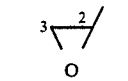 | |
| Q8 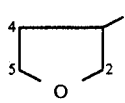 | Q22 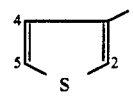 | |
| Q9 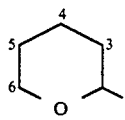 | Q23 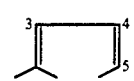 | |
| Q10 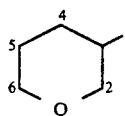 | Q24 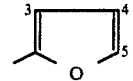 | |
| Q11 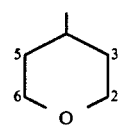 | Q25 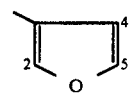 | |
| Q12 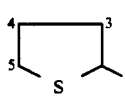 | Q26 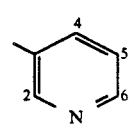 | |
| Q13 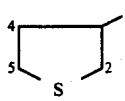 | Q27 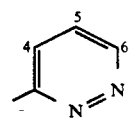 | |
| Q14 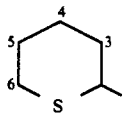 | | |

-continued
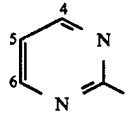 Q28
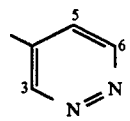 Q29
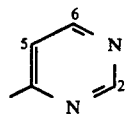 Q30
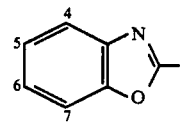 Q31
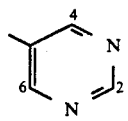 Q32
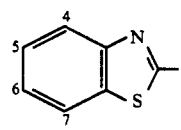 Q33
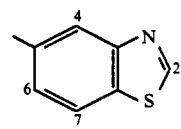 Q34
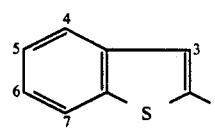 Q35
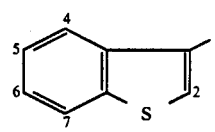 Q36
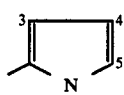 Q37
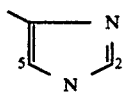 Q38
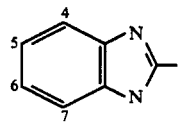 Q39
-continued
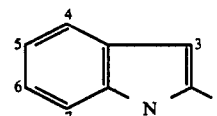 Q40
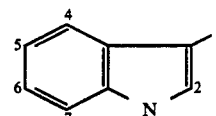 Q41
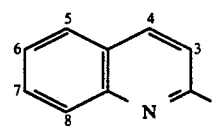 Q42
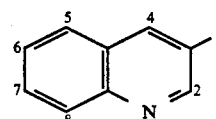 Q43
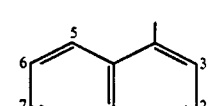 Q44
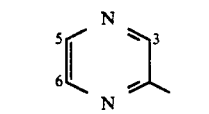 Q45
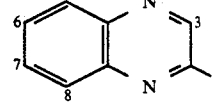 Q46
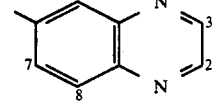 Q47
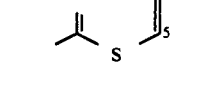 Q48
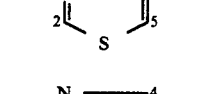 Q49
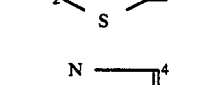 Q50
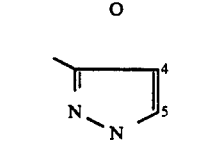 Q51
 Q52

-continued

Q53 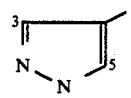

Q54 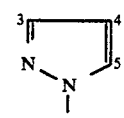

Q55 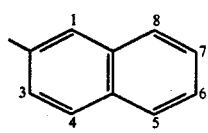

Q56 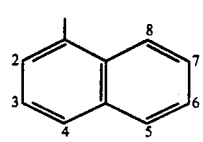

Q57 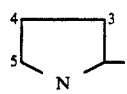

Q58 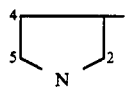

Q59 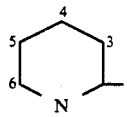

Q60 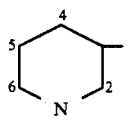

Q61 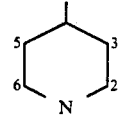

Q62 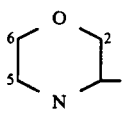

Q63 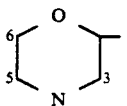

Q64 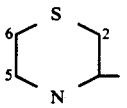

Q65 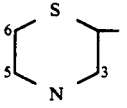

Q66 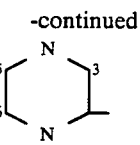

Q67 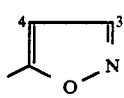

Q68 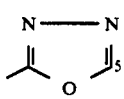

Q69 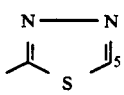

Q70 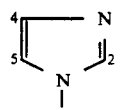

The preparations of the compounds of the present invention are described in detail by way of the following examples which are not intended to limit the scope the invention.

Preparation Example 1

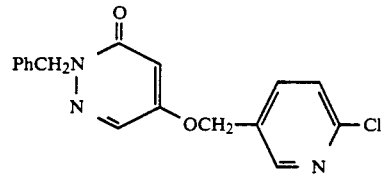

Synthesis of the compound No. 5 of the present invention.

In 20 ml of N,N-dimethylformamide were dissolved 1.2 g of 2-benzyl-5-hydroxy-3(2H)-pyridazinone and 1.3 g of 6-chloro-3-pyridinemethanolmesylate and 1.1 g of anhydrous potassium carbonate were added. The reaction mixture was heated and stirred for one hour in an oil bath of 70° C. After cooling to room temperature, the solution was poured into water, filtered off and washed with water. The crystals thus obtained were recrystalized from acetonitrile to give 760 mg of the intended compound.

melting point (m.p.): 161.7°–162.5 ° C.

Preparation Example 2

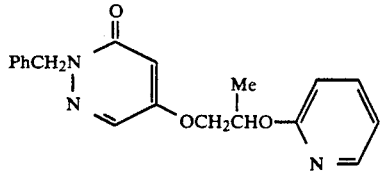

Synthesis of the compound No. 9 of the present invention

In 10 ml of N,N-dimethylformamide were dissolved 1.0 g of 2-benzyl-5-chloro-3(2H)-pyridazinone and 0.64 g of 2-(2-pyridyloxy)-1-propanol and 0.3 g of potassium hydroxide was added. The resulting solution was stirred for 24 hours at room temperature, then water was added and extracted with ethyl acetate. The organic layer of the extract was washed with water, dried over anhydrous sodium sulfate and freed of ethyl acetate by distillation under reduced pressure to obtain a brown oil. This oil was purified by means of column chromatography (on silica gel, eluting with benzene-ethyl acetate 3/1) to give 300 mg of the intended compound.

melting point: 75.3°–75.9 °C.

Preparation Example 3

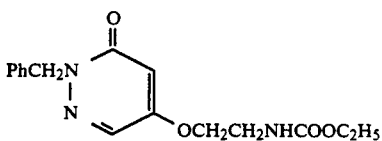

Synthesis of the compound No 32 of the present invention

In 20 ml of benzene, were dissolved 0.6 g of 5-(2-aminoethyloxy)-2-benzyl-3(2H)-pyridazinone (Compound No. 30 of the present invention), and thereto were added 1 ml of triethylamine and 0.3 g of ethyl chloroformate under ice-cooling. The resulting mixture was stirred for two hours at room temperature, washed with an aqueous solution of diluted hydrochloric acid, and then the benzene layer thereof was washed with water, dried and freed of benzene by distillation to give 0.5 g of white crystals of the compound of the present invention.

melting point: 73.5°–78.0 °C.

Preparation Example 4

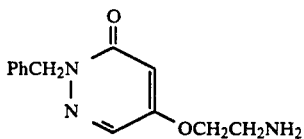

Synthesis of Compound No. 30 of the present invention

The mixture of 1.3 g of 55 % sodium hydride and 20 ml of N,N-dimethylformamide was ice-cooled, and 5.7 g of N-(2-hydroxyethyl) phthalimide was added. To the resulting solution was added 6.6 g of 2-benzyl-5-chloro-3(2H)-pyridazinone and kept for 24 hours at room temperature. To the resulting solution was added water, and then separated crystals were filtered off, washed with water and dried to give 7.9 g of 2-benzyl-5-[2-(phthalimidoyl)ethyloxy]-3(2H)-pyridazinone. The resulting raw crystals were mixed with 50 ml of methylene chloride and 3.5 g of hydrazine hydrate, heated at refluxing temperature for 4 hours for reacting, then after air-cooling the same the precipitated crystals were filtered off, and the filtered solution was washed with diluted aqueous alkali solution, and then the layer of methylene chloride was dried and the solvent was freed by distillation to obtain 3.8 g of raw crystals of the present invention.

melting point: 45°–59 °C.

Preparation Example 5

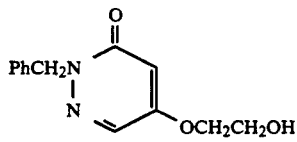

Synthesis of Compound No. 41 of the present invention

To the mixture of 5 g of 2-benzyl-5-chloro-3(2H)pyridazinone, 5.2 g of sodium hydroxide, 18.7 g of 2-bromoethyl alchohol and 20 ml of water was added a catalytic amount of tetrabutylanmmonium bromide and heated for 9 hours at refluxing temperature for reacting. After air-cooling the same, the solution was extracted with chloroform, and then the chloroform layer was washed with diluted aqueous alkali solution, the solution thus obtained was dried and the solvent was distilled off to obtain 3.6 g of raw crystals of the compound of the present invention.

Preparation Example 6

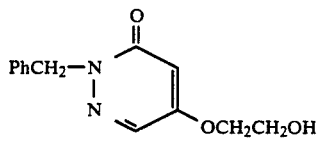

Synthesis of Compound No. 41 of the present invention

To 30 ml of N,N-dimethylformamide containing 0.43 g of 55% sodium hydride was added 2 g of 2-benzyl-5-hydroxy-3(2H)-pyridazinone, and then thereto was added 0.8 g of etylene carbonate and the solution was heated for 3 hours at 120° C. After cooling, to the solution was added water and the solution was extracted with ethyl acetate. After drying, the solvent was distilled off the to give 0.6 g of raw crystals of the compound of the present invention.

Preparation Example 7

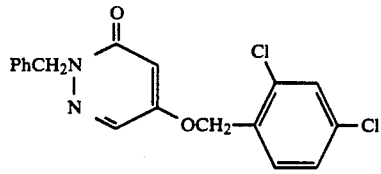

Synthesis of Compound No. 4 of the present invention

The mixture of 1.5 g of 2-benzyl-5-hydroxy-3(2H)pyridazinone, 1.5 g of 2,4-dichlorobenzyl chloride, 1.2 g of anhydrous potassium carbonate and 30 ml of N,N-dimethylformamide was heated for 4 hours at 130 °C. After cooling to room temperature, to the mixture was added water and the separated crystals were filtered off. Then, after the raw crystals thus obtained were washed with isopropylether, by recrystalizing from ethanol, 1.9 g of white crystals of the compound of the present invention were obtained.

melting point: 138°–140.2° C.

Preparation Example 8

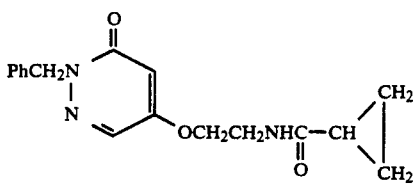

Synthesis of Compound No. 57 of the present invention

The mixture of 0.9 g of 5-(2-aminoethyloxy)-2-benzyl-3(2H)-pyridazinone (Compound No. 30 of the present invention), 0.4 g of triethylamine, 0.4 g of cyclopropanecarboxylic acid chloride and 30 ml of methylene chloride was heated and refluxed for 2 hours. After cooling to room temperature, the solution was washed with diluted aqueous hydrochloric acid solution and the layer of methylene chloride was dried and freed of the solvent to give raw crystals. The raw crystals thus obtained were purified by means of silica gel column chromatography (eluent: benzene/ethyl acetate 1/1) to give 0.8 g of a white crystal of the compound of the present invention.

melting point: 159.6°–161.2 ° C.

Preparation Example 9

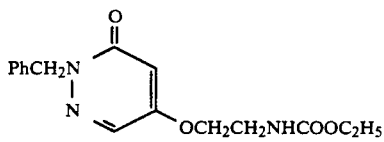

Synthesis of Compound No. 32 of the present invention

To the mixture of 1.0 g of 2-benzyl-5-hydroxy-3(2H)-pyridazinone, 0.9 g of ethyl N-(2-chloroethyl) carbamate ($ClCH_2CH_2NHCHO_2C_2H_5$), 1.4 g of anhydrous potassium carbonate and 30 ml of N,N-dimethylformamide was added a catalytic amount of potassium iodide and heated for 7 hours 70°–80 ° C. After the solvent was distilled off, to the residue was added with water and extracted with chloroform. After drying the chloroform layer, raw crystals thus obtained by distillation were washed with the mixed solvent of isopropylether/benzene to give 0.9 g of a white crystal of the compound of the present invention.

Preparation Example 10

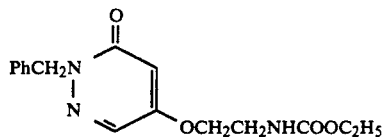

Synthesis of Compound No. 32 of the present invention

In 50 ml of ethanol was dissolved 1.0 g of 2-benzyl-4-chloro-5-(2-ethoxycarbonylamino)ethyloxy)-3(2H)-pyridazinone white crystal: melting point 122.5°–123.9 ° C.), and to this solution was added 5% paradium-carbon catalyst (Pd/c). The solution was strongly stirred in the hydrogeneous atmosphere to carry out the reaction of dechlorination of the 4 position. After a treatment, the reaction product thus obtained was repeated to be purified by means of a thin layer chromatography to give 0.1 g of a white crystal of the compound of the present invention.

Preparation Example 11

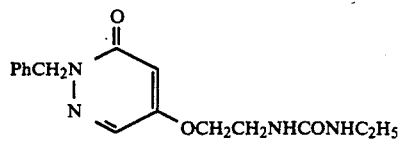

Synthesis of Compound No. 39 of the present invention

In 10 ml of benzene was dissolved 1.0 g of the compound No. 30 of the present invention, and to this solution was added 0.4 g of ethyl isocyanate ($C_2H_5NCO$), then the solution was stirred at room temperature to precipitate crystals. The crystals were filtered off and dried to give 0.9 g of white crystals of the compound of the present invention.

melting point: 169.0°–171.5 ° C.

Reference Example 1

Synthesis of 2-benzyl-5-hydroxy-3(2H)-pyridazinone

To the mixture of 60 g of 2-benzyl-4,5-dichloro-3(2H)-pyridazinone and 38.8 g of potassium hydroxide was added 250 ml of ethanol and 150 ml of water and heated in an oil bath to the refluxing temperature for 10 hours. After reaction the solvent was distilled off under reduced pressure, and to the residual solution was added 200 ml of water and washed twice with chloroform, the water layer was acidified with concentrated hydrochloric acid. The white solid thus separated was filtered off, washed with water and dried to obtain 55 g of 2-benzyl-4-chloro-5-hydroxy-3(2H)-pyridazinone. Subsequently, in aqueous sodium hydroxide solution (NaOH 1.82 g, water 20 ml) were added 5.0 g of 2-benzyl-4-chloro-5-hydroxy-3(2H)-pyridazinone and 200 mg of 5 % Pd/C , then 474 ml of hydrogen gas was absorbed in the solution under normal pressure. After reaction, Pd/C was filtered off and to the solution was added concentrated hydrochloric acid to be acidified. The white solid thus separated was filtered off, washed with water and dried to obtain 4.1 g of 2-benzyl-5-hydroxy-3(2H)-pyridazinone.

melting point: 48°–55 ° C.

Reference Example 2

Synthesis of 5-chloro-2-(cyclohexylmethyl)-3(2H)-pyridazinone

To 10.5 g of 2- (cyclohexylmethyl)-5-hydroxy-3(2H)-pyridazinone was added 25 ml of phosphorus oxychloride and this mixture was heated for 4 hours at 85° C. After reaction, the excess phosphorus oxychloride was distilled off under reduced pressure. The residual solution was poured into water and to this solution was added aqueous sodium hydroxide solution to be alkalified and the separated solid was extracted with benzene. The benzene layer was washed with water, dried over anhydrous sodium sulfate and filtered off with silica gel. Benzene was distilled off under reduced pressure to obtain 6.4 g of the intended compound.

melting point: 81.6°–81.8 ° C.

Reference Example 3

Synthesis of 2-benzyl-5-(3-hydroxypropyloxy)-3(2H)-pyridazinone

The mixture of 10 g of 2-benzyl-5-chloro-3(2H)-pyridazinone, 50 g of 1,3-propanediol, 3.0 g of 85 % potassium hydroxide and 50 ml of N,N-dimethylformamide was reacted for 24 hours at room temperature, then to the reaction solution was added water and extracted with ethyl acetate, dried and freed of solvent to obtain 9.4 g of the intended compound.

a white colored crystal melting point: 91°-93 ° C.

The physical properties of the compounds which were manufactured by the preparation methods illustrated in Preparation Examples 1 to 11 are shown in Table 2.

The compound Nos. of Table 2 correspond to those of the Formulation Examples and Test Examples.

TABLE 2

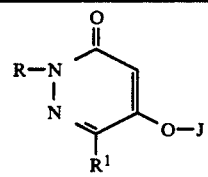

[I]

In the compound represented by the formula (I).

| No. | R | $R^1$ | J | m.p. (°C.) |
|---|---|---|---|---|
| 1 | PhCH$_2$ | H | CH$_2$C$_6$H$_4$(Et)-4 | 108.5–109.9 |
| 2 | PhCH$_2$ | H | CH$_2$C$_6$H$_4$(Cl)-4 | 126.5–127.9 |
| 3 | PhCH$_2$ | H | CH$_2$C$_6$H$_4$(I)-4 | 145.8–147.3 |
| 4 | PhCH$_2$ | H | CH$_2$C$_6$H$_3$(Cl$_2$)-2,4 | 138.2–140.2 |
| 5 | PhCH$_2$ | H | CH$_2$(Q26-Cl-6) | 161.7–162.5 |
| 6 | PhCH$_2$ | H | CH$_2$(Q26-I-6) | 173.6–174.8 |
| 7 | PhCH$_2$ | H | CH$_2$CH$_2$OPh | 102.8–103.6 |
| 8 | PhCH$_2$ | H | CH$_2$CH$_2$O(Q17) | 110.4–111.3 |
| 9 | PhCH$_2$ | H | CH$_2$CH(Me)O(Q17) | 75.3–75.9 |
| 10 | PhCH$_2$ | H | CH$_2$CH=NOPr | 71–72 |
| 11 | PhCH$_2$ | H | CH$_2$CH$_2$ON=CHMe | 84–86 |
| 12 | PhCH$_2$ | H | CH$_2$COOMe | 118.4–120.2 |
| 13 | PhCH$_2$ | H | CH$_2$CONH$_2$ | 275–278 |
| 14 | PhCH$_2$ | H | CH$_2$CH(OEt)$_2$ | oily* |
| 15 | (Q4)CH$_2$ | H | CH$_2$(Q26-I-6) | 156.9–157.9 |
| 16 | (Q4)CH$_2$ | H | CH$_2$CH$_2$OPh | 91.8–92.9 |
| 17 | (Q4)CH$_2$ | H | CH$_2$CH(Me)O(Q17) | 117.5–118.3 |
| 18 | (Q4)CH$_2$ | H | CH$_2$C(Me)=NOPr | $N_D^{20}$ = 1.5198 |
| 19 | 3-MeC$_6$H$_4$CH$_2$ | H | CH$_2$(Q26-Cl-6) | 144.5–146.5 |
| 20 | 3-ClC$_6$H$_4$CH$_2$ | H | CH$_2$(Q26-Cl-6) | 163.0–163.6 |
| 21 | 2,4-F$_2$C$_6$H$_3$CH$_2$ | H | CH$_2$(Q26-I-6) | 161.3–162.4 |
| 22 | PhCH$_2$ | H | CH$_2$CO$_2$H | white crystal* |
| 23 | PhCH$_2$ | H | CH$_2$CO$_2$Et | 87.5–89.0 |
| 24 | PhCH$_2$ | H | CH$_2$CO$_2$Pr-i | $N_D^{23.5}$ = 1.5355 |
| 25 | PhCH$_2$ | H | CH$_2$CO$_2$Bu | $N_D^{20}$ = 1.5353 |
| 26 | PhCH$_2$ | H | CH$_2$CO$_2$Bu-t | 76–78 |
| 27 | PhCH$_2$ | H | CH$_2$CONHEt | 127–128 |
| 28 | PhCH$_2$ | H | CH$_2$CONHPr | 142–144 |
| 29 | PhCH$_2$ | H | CH$_2$CONHBu | 123.5–125.0 |
| 30 | PhCH$_2$ | H | CH$_2$CH$_2$NH$_2$ | 45–59* |
| 31 | PhCH$_2$ | H | CH$_2$CH$_2$NHCO$_2$Me | 110.0–111.5 |
| 32 | PhCH$_2$ | H | CH$_2$CH$_2$NHCO$_2$Et | 73.5–78.0 |
| 33 | PhCH$_2$ | H | CH$_2$CH$_2$NHCO$_2$Pr | 77.0–79.5 |
| 34 | PhCH$_2$ | H | CH$_2$CH$_2$NHCO$_2$Pr-i | 114.9–117.3 |
| 35 | 2,4-F$_2$C$_6$H$_3$CH$_2$ | H | CH$_2$CH$_2$NHCO$_2$Et | 111.7–112.6 |
| 36 | PhCH$_2$ | H | CH$_2$CH$_2$NHCO$_2$Ph | 129.8–132.6 |
| 37 | PhCH$_2$ | H | CH$_2$CH$_2$NHCOPr | 113.0–118.0 |
| 38 | PhCH$_2$ | H | CH$_2$CH$_2$NHCOPh | 147.0–147.9 |
| 39 | PhCH$_2$ | H | CH$_2$CH$_2$NHCONHEt | 169.0–171.5 |
| 40 | PhCH$_2$ | H | CH$_2$CH$_2$NHCONMe$_2$ | 107.6–108.9 |
| 41 | PhCH$_2$ | H | CH$_2$CH$_2$OH | white crystal* |
| 42 | PhCH$_2$ | H | CH$_2$CH$_2$OCONHEt | 128.5–129.0 |
| 43 | PhCH$_2$ | H | CH$_2$CH$_2$OCONHPr-i | 132.2–133.1 |
| 44 | PhCH$_2$ | H | CH$_2$CH$_2$OCONHPh | 169.3–170.5 |
| 45 | 3-MeC$_6$H$_4$CH$_2$ | H | CH$_2$CH$_2$O(Q17) | 85.0–87.0 |
| 46 | 3-ClC$_6$H$_4$CH$_2$ | H | CH$_2$CH$_2$O(Q17) | 122.8–123.7 |
| 47 | 2,4-F$_2$C$_6$H$_3$CH$_2$ | H | CH$_2$CH$_2$O(Q17) | 116.4–117.3 |
| 48 | PhCH$_2$ | H | CH$_2$CH$_2$O(Q27) | 140–142 |
| 49 | PhCH$_2$ | H | (CH$_2$)$_3$C≡CMe | 104.6–105.4 |
| 50 | PhCH$_2$ | H | CH$_2$CH$_2$OBu-i | 66.7–67.9 |
| 51 | PhCH$_2$ | H | CH$_2$CH$_2$CH(OEt)$_2$ | oily* |
| 52 | PhCH$_2$ | H | CH$_2$CH$_2$NHSO$_2$Et | 88–94.2 |
| 53 | PhCH$_2$ | H | CH$_2$CH$_2$NHSO$_2$SO$_2$NMe$_2$ | 80.7–88.2 |
| 54 | PhCH$_2$ | H | CH$_2$CH$_2$NHC(O)SEt | 95.9–127.8 |
| 55 | PhCH$_2$ | H | CH$_2$CH$_2$NHCOC(Me)=CH$_2$ | 120.0–122.9 |
| 56 | PhCH$_2$ | H | CH$_2$CH$_2$NHCOCH=C(Me)$_2$ | 110.3–110.8 |
| 57 | PhCH$_2$ | H | CH$_2$CH$_2$NHCO(Q1) | 159.5–161.2 |
| 58 | PhCH$_2$ | H | (CH$_2$)$_3$OCONHEt | 122.1–122.6 |
| 59 | PhCH$_2$ | H | (CH$_2$)$_3$NHCO$_2$Et | 112.4–113.1 |

TABLE 2-continued

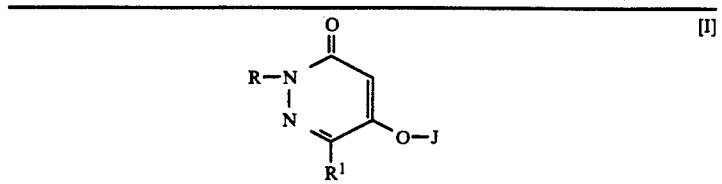

In the compound represented by the formula (I).

| No. | R | R$^1$ | J | m.p. (°C.) |
|---|---|---|---|---|
| 60 | PhCH$_2$ | H | (CH$_2$)$_3$NHCO$_2$Me | 107.2–108.0 |
| 61 | PhCH$_2$ | H | CH$_2$CH$_2$OCO(Q1) | 72.2–73.5 |
| 62 | PhCH$_2$ | H | (CH$_2$)$_3$OCO(Q1) | 74.2–75.4 |
| 63 | 3-CF$_3$C$_6$H$_4$CH$_2$ | H | CH$_2$CH$_2$O(Q17) | 99.4–100.3 |
| 64 | 3-CF$_3$C$_6$H$_4$CH$_2$ | H | CH$_2$(Q26-Cl-6) | 167.8–168.9 |
| 65 | 3,5-Cl$_2$C$_6$H$_3$CH$_2$ | H | CH$_2$CH$_2$O(Q17) | 120.0–122.0 |
| 66 | 3,5-Cl$_2$C$_6$H$_3$CH$_2$ | H | CH$_2$(Q26-I-6) | 175.7–176.6 |
| 67 | 3-CF$_3$C$_6$H$_4$CH$_2$ | H | CH$_2$CH$_2$NHCO$_2$Me | 114.3–115.0 |
| 68 | 3-CF$_3$C$_6$H$_4$CH$_2$ | H | CH$_2$CH$_2$NHCO$_2$Et | 102.8–103.6 |
| 69 | 3-CF$_3$C$_6$H$_4$CH$_2$ | H | CH$_2$CH$_2$NHCO(Q1) | 152.1–152.6 |
| 70 | PhCH$_2$ | H | (CH$_2$)$_3$NHCO(Q1) | 182.0–184.0 |
| 71 | 3,5-Cl$_2$C$_6$H$_3$CH$_2$ | H | CH$_2$CH$_2$NHCO$_2$Et | 126.0–129.0 |
| 72 | PhCH$_2$ | H | CH$_2$CH(Me)NHCO$_2$Et | |
| 73 | PhCH$_2$ | H | CH(Me)CH$_2$NHCO(Q1) | |
| 74 | 3-BrC$_6$H$_4$CH$_2$ | H | CH$_2$(Q26-Cl-6) | |
| 75 | 3-BrC$_6$H$_4$CH$_2$ | H | CH$_2$CH$_2$O(Q17) | 127.9–128.4 |
| 76 | 3-BrC$_6$H$_4$CH$_2$ | H | CH$_2$CH$_2$NHCO$_2$Et | |
| 77 | 3-BrC$_6$H$_4$CH$_2$ | H | CH$_2$(Q26-I-6) | 175.8–176.8 |
| 78 | 3-BrC$_6$H$_4$CH$_2$ | H | CH$_2$CH$_2$NHCO(Q1) | |
| 79 | 3-FC$_6$H$_4$CH$_2$ | H | CH$_2$(Q26-I-6) | 162.6–164.0 |
| 80 | 3-FC$_6$H$_4$CH$_2$ | H | CH$_2$CH$_2$NHCO$_2$Et | 83.5–84.5 |
| 81 | 3-FC$_6$H$_4$CH$_2$ | H | CH$_2$CH$_2$NHCO(Q1) | 147.3–148.3 |
| 82 | 3-FC$_6$H$_4$CH$_2$ | H | CH$_2$CH$_2$O(Q17) | 103.5–104.3 |
| 83 | 4-ClC$_6$H$_4$CH$_2$ | H | CH$_2$(Q26-I-6) | |
| 84 | 4-ClC$_6$H$_4$CH$_2$ | H | CH$_2$CH$_2$NHCO$_2$Et | |
| 85 | 4-ClC$_6$H$_4$CH$_2$ | H | CH$_2$CH$_2$NHCO(Q1) | |
| 86 | 4-ClC$_6$H$_4$CH$_2$ | H | CH$_2$CH$_2$O(Q17) | |
| 87 | 2-ClC$_6$H$_4$CH$_2$ | H | CH$_2$(Q26-Cl-6) | |
| 88 | 2-ClC$_6$H$_4$CH$_2$ | H | CH$_2$CH$_2$NHCO$_2$Et | |
| 89 | 2-ClC$_6$H$_4$CH$_2$ | H | CH$_2$CH$_2$NHCO(Q1) | |
| 90 | 3-NO$_2$C$_6$H$_4$CH$_2$ | H | CH$_2$(Q26-Cl-6) | |
| 91 | 3-NO$_2$C$_6$H$_4$CH$_2$ | H | CH$_2$CH$_2$NHCO$_2$Et | |
| 92 | 3-NO$_2$C$_6$H$_4$CH$_2$ | H | CH$_2$CH$_2$NHCO(Q1) | |
| 93 | (Q17)CH$_2$ | H | CH$_2$(Q26-Cl-6) | |
| 94 | (Q17)CH$_2$ | H | CH$_2$CH$_2$NHCO$_2$Et | |
| 95 | (Q17)CH$_2$ | H | CH$_2$CH$_2$NHCO$_2$Me | |
| 96 | (Q17)CH$_2$ | H | CH$_2$CH$_2$NHCO(Q1) | |
| 97 | (Q17)CH$_2$ | H | CH$_2$CH$_2$O(Q17) | |
| 98 | (Q26)CH$_2$ | H | CH$_2$CH$_2$O(Q17) | 120.0–121.5 |
| 99 | (Q26)CH$_2$ | H | CH$_2$CH$_2$NHCO$_2$Et | |
| 100 | (Q26)CH$_2$ | H | CH$_2$CH$_2$NHCO(Q1) | |
| 101 | (Q26-Cl-6)CH$_2$ | H | CH$_2$CH$_2$NHCO$_2$Et | |
| 102 | (Q26-Cl-6)CH$_2$ | H | CH$_2$CH$_2$NHCO(Q1) | |
| 103 | (Q17-CF$_3$5)CH$_2$ | H | CH$_2$CH$_2$NHCO$_2$Et | |
| 104 | (Q17-CF$_3$-5)CH$_2$ | H | CH$_2$CH$_2$NHCO(Q1) | |
| 105 | (Q18)CH$_2$ | H | CH$_2$(Q26-Cl-6) | |
| 106 | (Q18)CH$_2$ | H | CH$_2$CH$_2$O(Q17) | |
| 107 | (Q18)CH$_2$ | H | CH$_2$CH$_2$NHCO$_2$Et | |
| 108 | (Q18)CH$_2$ | H | CH$_2$CH$_2$NHCO(Q1) | |
| 109 | PhCH$_2$ | H | CH$_2$(Q17-CF$_3$-5) | |
| 110 | 3-ClC$_6$H$_4$CH$_2$ | H | CH$_2$(Q17-CF$_3$-5) | |
| 111 | PhCH(Me) | H | CH$_2$(Q26-Cl-6) | |
| 112 | PhCH(Me) | H | CH$_2$CH$_2$O(Q17) | $N_D^{27}$ = 1.5846 |
| 113 | PhCH(Me) | H | CH$_2$CH$_2$NHCO$_2$Et | 85–86 |
| 114 | PhCH(Me) | H | CH$_2$CH$_2$NHCO(Q1) | |
| 115 | PhCH$_2$CH$_2$ | H | CH$_2$(Q26-I-6) | 163.9–164.7 |
| 116 | PhCH$_2$CH$_2$ | H | CH$_2$CH$_2$O(Q17) | 117.9–119.4 |
| 117 | PhCH$_2$CH$_2$ | H | CH$_2$CH$_2$NHCO$_2$Et | 85–87 |
| 118 | PhCH$_2$CH$_2$ | H | CH$_2$CH$_2$NHCO(Q1) | 162.6–163.2 |
| 119 | PhCH$_2$ | H | CH$_2$(Q67-Me-3) | |
| 120 | PhCH$_2$ | H | CH$_2$(Q67-Br-3) | 111.7–112.6 |
| 121 | PhCH$_2$ | H | CH$_2$[Q67-(Q1)-3] | |
| 122 | 3-ClC$_6$H$_4$CH$_2$ | H | CH$_2$(Q67-Me-3) | |
| 123 | 3-ClC$_6$H$_4$CH$_2$ | H | CH$_2$(Q67-Br-3) | |
| 124 | 3-FC$_6$H$_4$CH$_2$ | H | CH$_2$[Q67-(Q1)-3] | |
| 125 | 3-FC$_6$H$_4$CH$_2$ | H | CH$_2$(Q67-Me-3) | |
| 126 | 3-FC$_6$H$_4$CH$_2$ | H | CH$_2$(Q67-Br-3) | 84.5–85.5 |
| 127 | 3-BrC$_6$H$_4$CH$_2$ | H | CH$_2$(Q67-Me-3) | |
| 128 | 3-BrC$_6$H$_4$CH$_2$ | H | CH$_2$(Q67-Br-3) | 119.9–121.2 |
| 129 | 3-CF$_3$C$_6$H$_4$CH$_2$ | H | CH$_2$(Q67-Me-3) | |

TABLE 2-continued

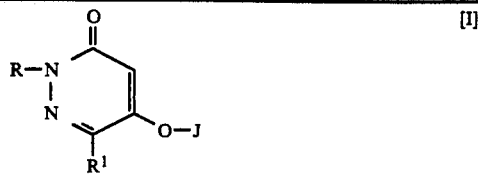

In the compound represented by the formula (I).

| No. | R | R¹ | J | m.p. (°C.) |
|---|---|---|---|---|
| 130 | 3-CF$_3$C$_6$H$_4$CH$_2$ | H | CH$_2$(Q67-Br-3) | 99–103 |
| 131 | 3,5-Cl$_2$C$_6$H$_3$CH$_2$ | H | CH$_2$(Q67-Me-3) | |
| 132 | 3,5-Cl$_2$C$_6$H$_3$CH$_2$ | H | CH$_2$(Q67-Br-3) | 160.1–162.1 |
| 133 | 3,5-Cl$_2$C$_6$H$_3$CH$_2$ | H | CH$_2$[Q67-(Q1)-3] | |
| 134 | PhCH$_2$ | H | CH$_2$(Q67-Cl-3) | |
| 135 | 3-ClC$_6$H$_4$CH$_2$ | H | CH$_2$(Q67)-Cl-3) | |
| 136 | 3-FC$_6$H$_4$CH$_2$ | H | CH$_2$(Q67-Cl-3) | |
| 137 | 3-BrC$_6$H$_4$CH$_2$ | H | CH$_2$(Q67-Cl-3) | |
| 138 | 3-CF$_3$C$_6$H$_4$CH$_2$ | H | CH$_2$(Q67-Cl-3) | |
| 139 | 3,5-Cl$_2$C$_6$H$_3$CH$_2$ | H | CH$_2$(Q67-Cl-3) | |
| 140 | PhCH$_2$ | H | CH$_2$(Q67-I-3) | |
| 141 | 3-NO$_2$C$_6$H$_4$CH$_2$ | H | CH$_2$(Q26-I-6) | 184–186 |
| 142 | PhCH(Me) | H | CH$_2$(Q26-I-6) | 124–127 |
| 143 | PhCH$_2$CH$_2$ | H | CH$_2$CH=NOPr | 82.7–84.0 |
| 144 | 3-NO$_2$C$_6$H$_4$CH$_2$ | H | CH$_2$CH$_2$O(Q17) | 122–123 |
| 145 | PhCH$_2$ | H | (CH$_2$)$_3$CO$_2$Et | |
| 146 | PhCH$_2$ | H | CH$_2$CH$_2$O(Q28) | 98.3–99.7 |
| 147 | 3-CF$_3$C$_6$H$_4$CH$_2$ | H | CH$_2$[Q67-(Q1)-3] | |
| 148 | PhCH$_2$ | H | CH$_2$CH$_2$F | 93.8–94.9 |

Each data of NMR for the compound Nos. 14, 22, 30, 41 and 51 in Table 2 is as follows.
Compound No. 14
NMR (CDCl$_3$, δ value): 1.19(6H, t, J=7Hz), 3.58(2H, q, J=7Hz), 3.62(2H, q, J=7Hz), 3.86(2H, d, J=5Hz), 4.70(1H, t, J=5Hz), 5.14(2H, s), 6.02(1H, d, J=2.4Hz), 7.0~7.4(5H, m), 7.60(1H, d, J=2.4Hz).
Compound No. 22
NMR (DMSO-d$_6$, δ value): 4.58(2H, s), 5.27(2H, s), 6.15(1H, m), 7.37(5H, s), 7.70(1H, m), 9.8(1H, bs).
Compound No. 30
NMR (CDCl$_3$, δ value): 1.45(2H, bs), 3.05(2H, t), 3.92(2H, t), 5.25(2H, s), 6.10(1H, d), 7.35(5H, s), 7.60(1H, d).
Compound No. 41
NMR (CDCl$_3$, δ value): 3.5(1H, bs), 4.00(4H, s), 5.30(2H, s), 6.20(1H, d), 7.40(5H, s), 7.65(1H, d).
Compound No. 51
NMR (CDCl$_3$, δ value): 1.20(6H, 6), 2.10(2H, m), 3.4~3.8(4H, m), 4.00(2H, t), 4.66(1H, t), 5.25(2H, s), 6.14(1H, d), 7.32(5H, s), 7.55(1H, d).

When the compounds according to the present invention are used for compositions for preventing and controlling insect pests, they are generally mixed with suitable carriers, for instance, solid carriers such as clay, talc, bentonite or diatomaceous earth, or liquid carriers such as water, alcohols (e.g., methanol and ethanol), aromatic hydrocarbons (e.g., benzene, toluene and xylene), chlorinated hydrocarbons, ethers, ketones, esters (e.g., ethyl acetate) or acid amides (e.g., dimethylformamide). If desired, to these mixtures may be added emulsifier, dispersing agent, suspension agent, penetrating agent, spreader, stabilizer and the like to put them into practical use in the form of emulsifiable concentrate, oil solution, wettable powder, dust, granule, Moreover, the mixtures may be incorporated, as necessary, with other insecticides, various herbicides fungicides, plant-growth regulating agents, synergists in formulations or applications thereof.

The amount of the compounds of the invention to be used as an active ingredient is suitably in the range of 0.005 to 50 kg per hectare although it varies depending upon the place and the seasons where the compounds are applied, manner of application, diseases and insect pests to be applied, cultivated crops to be protected and the like.

The following is a formulation proportion and kinds of various preparations of the present invention.

| | Active ingredient | Carrier | Surface-active agent | Other component (adjuvant) |
|---|---|---|---|---|
| Emulsifiable concentrates | 1–25 | 52–95 | 3–20 | 0–20 |
| Oil solutions | 1–30 | 70–99 | | |
| Flowables | 1–70 | 10–90 | 1–20 | 0–10 |
| Wettable powders | 1–70 | 15–93 | 3–10 | 0–5 |
| Dusts | 0.01–30 | 67–99.5 | | 0–3 |
| Granules | 0.01–30 | 67–99.5 | | 0–8 |
| Granule-shaped wettable powder | 1–90 | 5–90 | 1–50 | 0–30 |

The numeral values in the above table represent "percent by weight".

In use, emulsifiable concentrates, oil solutions, flowables, wettable powder and granule-shaped wettable powder are diluted with a predetermined amount of water and applied. Dusts and granules are directly applied without being diluted with water. The granules contain baits.

Each component of the above formulations is exemplified as follows.

Emulsifiable concentrates
Active ingredient: Present compound
Carrier: xylene, dimethylformamide,

|                      | -continued |
|----------------------|------------|
|                      | methylnaphthalene, cyclohexanone, dichlorobenzene, isophorone |
| Surface-active agent: | Sorpol 2680, Sorpol 3005X, Sorpol 3353 |
| Other ingredients:   | piperonylbutoxide, benzotriazole |
| Oil solution         |            |
| Active ingredient:   | Present compound |
| Carrier:             | xylene, methylcellosolve, kerosene |
| Flowables            |            |
| Active ingredient:   | Present compound |
| Carrier:             | water |
| Surface-active agent: | Lunox 1000C, Sorpol 3353, Soprophor FL, Nippol, Agrisol S-710, sodium lignin sulfonate |
| Other ingredients:   | Xanthan gum, formalin, ethylene glycol, propylene glycol |
| Wettable powders     |            |
| Active ingredient:   | Present compound |
| Carrier:             | calcium carbonate, kaolinite, Zeeklite D, Zeeklite PFP, diatomaceous earth, talc |
| Surface-active agent: | Sorpol 5039, Lunox 1000C, calcium lignin sulfonate, sodium dodecyl benzenesulfonate, Sorpol 5050, Sorpol 005D, Sorpol 5029-0 |
| Other ingredient:    | Carplex #80 |
| Dusts                |            |
| Active ingredient:   | Present compound |
| Carrier:             | calcium carbonate, kaolinite, Zeeklite D, talc |
| Other ingredient:    | diisopropyl phosphate, Carplex #80 |
| Granules (1)         |            |
| Active ingredient:   | Present compound |
| Carrier:             | calcium carbonate, kaolinite, bentonite, talc |
| Other ingredients:   | calcium lignin sulfonate, polyvinyl alcohol |
| Granules (2) (Bait)  |            |
| Active ingredient:   | Present compound |
| Carrier:             | wheat flour, wheat bran, corn grits, Zeeklite D |
| Other ingredients:   | paraffin, bean oil |
| Granule-shaped wettable powder |  |
| Active ingredient:   | Present compound |
| Carrier:             | calcium carbonate, kaolinite, Zeeklite, clay, ammonium sulfate, urea, white carbon |
| Surface-active agent: | Lunox 1000C, formarin-condensation agent of naphthalenesulfonate, polyoxyethylene-nonylphenylether, sodium lignin sulfonate |
| Other ingredient:    | stabilizer such as epoxidized bean oil, anti-oxidant |

In the following, there are shown formulation examples of compositions for preventing and controlling insect pests, said compositions containing the compounds of the present invention as an active ingredient. These examples are only illustrative and not to restrict the present invention. In the following formulation examples, "part" means "part by weight".

| Formulation Example 1: Emulsifiable concentrate | |
|---|---|
| Present compound: | 5 parts |
| Xylene | 70 parts |
| N,N-dimethylformamide | 20 parts |
| Sorpol 2680 (trade name: a mixture of a non-ionic surface-active agent and an anionic surface-active agent manufactured by Toho Chemical, Co., Ltd., Japan) | 5 parts |

In the above respective emulsifiable concentrates, each component of the respective emulsifiable concentrates are mixed intimately to form respective emulsifiable concentrates. Upon use, the emulsifiable concentrates are diluted with water up to one fiftieth to one twenty thousandth in concentration and applied to a rate of 0.005 to 50 kg of the active ingredient per hectare.

| Formulation Example 2: Wettable powders | |
|---|---|
| Present compound | 25 parts |
| Zeeklite PFP (trade name, a mixture of kaolinite and sericite manufactured by Zeeklite Mining Industries, Co., Ltd. | 66 parts |
| Sorpol 5039 (trade name, anionic surface-active agent manufactured by Toho Chemical, Co., Ltd., Japan) | 4 parts |
| Carplex #80 (trade name, white carbon manufactured by Shionogi Seiyaku K.K., Japan) | 3 parts |
| Calcium lignin sulfonate | 2 parts |

In the above respective wettable powders, each components of the respective wettable powders are intimately mmixed and ground to form respective wettable powder. Upon use, the wettable powders are diluted with water up to one fiftieth to one twenty thousandth in concentration and applied at a rate of 0.005 to 50 kg of the active ingredient per hectare.

| Formulation Example 3: Oil solutions | |
|---|---|
| Present compound | 10 parts |
| Methylcellosolve | 90 parts |

In the above respective oil solutions, each component of the respective oil solutions are homogeneously mixed together to form the respective oil solutions. Upon use, the oil solutions are applied at a rate of 0.005 to 50 kg of the active ingredient per hectare.

| Formulation Example 4: Dusts | |
|---|---|
| Present compound | 3.0 parts |
| Carplex #80 (trade name, white carbon manufactured by Shionogi Seiyaku K.K., Japan) | 0.5 part |
| Clay | 95.5 parts |
| diisopropyl phosphate | 1.5 parts |

In the above respective dusts, components of the respective dusts are homogeneously mixed together to form the respective dusts. Upon use, the dusts are applied at a rate of 0.005 to 50 kg of the active ingredient per hectare.

| Formulation Example 5: Granules | |
|---|---|
| Present compound | 5 parts |
| Bentonite | 54 parts |
| Talc | 40 parts |
| Calcium lignin sulfonate | 1 part |

In the above granules, components of granules are mixed intimately together and ground, incorporated with a small amount of water and mixed together with stirring. The resulting mixture is granulated by means of extrusion-granulator and dried to form granules. Upon use, the granule is applied to at a rate of 0.005 to 50 kg of the active ingredient per hectare.

| Formulation Example 6: Flowables | |
| --- | --- |
| Present compound | 35 parts |
| Sorpol 3353 (trade name, non-ionic surface-active agent manufactured by Toho Chemicals, Co., Ltd., Japan) | 10 parts |
| Lunox 1000C (trade name, as anionic surface-active agent manufactured by Toho Chemicals, Co., Ltd., Japan) | 0.5 part |
| 1% aqueous solution of Xanthan gum (natural high-molecular compound) | 20 parts |
| Water | 34.5 parts |

In the above respective flowables, each component except the active ingredient (present compound) are uniformly mixed together to form a solution. The resulting mixture is added to the present compound, thoroughly stirred and wet-ground by means of sand mill to form respective flowables. Upon use, the flowables are diluted up to one fiftieth to one twenty thousandth with water and applied at a rate of 0.005 to 50 kg of the active ingredient per hectare.

| Formulation Example 7: Granule-shaped wettable powder | |
| --- | --- |
| Present compound | 50 parts |
| Clay | 10 parts |
| Ammonium sulfate | 20 parts |
| Sodium lignin sulfonate | 10 parts |
| Formalin-condensation product of naphthalene sulfonate | 10 parts |

The components are uniformly mixed and ground and kneaded with water and then, subjected to an extruding granulator having a screen of 0.5 mm $\phi$ to be granulated. The water of the granulated product is dried to produce granule-shaped wettable powder. Upon use, the granule-shaped wettable powder is applied at a rate of 0.005 to 50 kg of the active ingredient per hectare.

In the following, the effects of the present compounds as an insecticide are explained in detail by way of the test examples.

Test Example 1

Insecticidal test on Green rice leafhopper (*Nephotettix cincticeps*)

A 5% emulsifiable concentrate (or a 25% wettable powder) of a compound of the present invention was diluted with water containing a spreader to give a 500 ppm solution of the compound.

The stems and leaves of rice-plant in a 1/20000 are pot were sufficiently applied with the resulting solution and then air-dried. Thereafter, 20 second instar nymphae of green rice leafhopper (*Nephotettix cincticeps*) which resist organic phosphorous insecticides and carbamate insecticides were released in the pot.

The rice-plant thus treated was covered with a cylindrical wire gauze and kept in a thermostatic chamber.

Thirty (30) days after, the number of the green rice leafhoppers parasitic on the rice-plant was counted and the mortality thereof was determined according to the following equation:

$$\text{Mortality (\%)} = \frac{\text{number of the insect killed}}{\text{number of insect released}} \times 100$$

The test was conducted twice for each compound. In the results, the following compounds exhibited high effects of 100% of mortality.

Compound Nos 2, 3, 5, 6, 11, 19, 20, 31, 66.

Test Example 2

Insecticidal test on Brown rice planthopper (*Nilaparvata lugens*)

The procedures in Test Example 1 were repeated by using second instar nymphae of brown rice planthopper (*Nilaparvata lugens*) instead of the second instar nymphae of green rice leafhoppers which resist organic phosphorous insecticides and carbamate insecticides. As a result, the following compounds exhibited high effects of 100% of mortality.

Compound Nos. 5, 6, 19, 20, 31, 32, 33, 35, 38, 39, 40, 42, 43, 44, 52, 53, 54, 56, 57, 59, 61, 65, 66.

Test Example 3

Insecticidal test on Red flour beetle (*Tribolium castaneum*)

In a transparent small test tube was placed 5% emulsifiable concentrate of a compound of the present invention (or a 25% wettable powder or a 20% oil solution thereof), and thereto was added acetone to give a 500 ppm acetone solution of the compound. Ten (10) cc of the acetone solution was added to 10 g of wheat flour placed in a laboratory dish of 9 cm in diameter. After stirring, acetone was distilled away from the mixture. Then, 10 adults each of male and female red flour beetle (*Tribolium castaneum*) were released in the dish. The dish containing the adults was kept in a thermostatic chamber.

Ninety (90) days after, evaluation was conducted by counting the number of the adults which came out.

The test was conducted twice of each compound.

As a result, no emerged adult was observed at all in the dish treated with any one of the following compounds. Compound Nos. 1, 2, 3, 5, 6, 7, 8, 9, 10, 11, 19, 20, 21, 31, 32, 33, 34, 35, 38, 39, 40, 42, 43, 44, 45, 46, 47, 50, 54, 56, 57, 63, 64, 65, 66.

Test Example 4

Insecticidal test on House mosquito (*Culex pipiens pallens*)

A 5% emulsifiable concentrate (or a 25% wettbble powder or 20% oil solution) of a compound of the present invention was diluted with deionized water to give a 10 ppm solution of the compound.

Two hundred (200) ml of the solution was poured in a tall laboratory dish of 9 cm in diameter and 6 cm in height. Ten larvae of house mosquito (*Culex pipiens pallens*) were released in the dish. The dish containing the larvae was kept in a thermostatic chamber of 25 ° C.

Seven (7) days after, the number of the larvae killed was counted.

The test was conducted twice of each compound.

As a result, no emerged adult was observed at all in the dish treated with any one the following compounds.

Compound Nos. 1, 3, 5, 6, 7, 8, 9, 10, 11, 20, 21, 24, 26, 27, 28, 42, 43, 45, 46, 47, 50, 54, 57, 63, 64, 65, 66.

Test Example 5

Insecticidal test on Almond moth (*Cadra cautella*)

In a transparent small test tube was placed 5% emulsifiable concentrate of a compound of the present invention (or a 25% wettable powder or a 20% oil solution thereof), and thereto was added acetone to give a 500 ppm acetone solution of the compound. Ten (10) cc of the acetone solution was added to 10 g of rice bran placed in a laboratory dish of 9 cm in diameter. After stirring, acetone was distilled away from the mixture. Then, 10 larvae of almond moth (*Cadra cautella*) were released in the dish. The dish containing the larvae was kept in a thermostatic chamber.

Thirty (30) days after, evaluation was conducted by counting the number of the adults which came out.

The test was conducted twice of each compound.

As a result, no emerged adult was observed at all in the dish treated with any one of the following compounds. Compound Nos. 1, 2, 3, 5, 6, 7, 8, 9, 10, 11, 19, 20, 21, 31, 32, 33, 34, 35, 36, 37, 38, 39, 42, 43, 44, 45, 46, 47, 49, 50, 52, 53, 54, 56, 57, 63, 64, 65, 66.

Test Example 6

Insecticidal test on Diamond back moth (*Plutella xylostella*)

A 5% emulsifiable concentrate (or a 25% wettable powder) of a compound of the present invention was diluted with water containing a spreader to give a 500 ppm solution of the compound.

Leaves of cabbage (*Brassica oleracea*) were dipped in the solution, air-dried and then put in a laboratory dish of 7 cm in diameter. Ten (10) third instar larvae of diamond back moth (*Plutella xylostella*) were released in each laboratory dish and kept in a thermostatic chamber.

Twenty (20) days after, the number of emerged adults was counted and the mortality thereof was determined according to the equation as described in Test Example 1. The test was conducted twice of each compound.

As a result, the following compounds exhibited high effects of 100% of mortality. Compound Nos. 1, 2, 3, 4, 5, 6, 11, 19, 20, 21, 31, 32, 33, 34, 35, 36, 37, 38, 39, 42, 43, 44, 45, 46, 47, 49, 50, 52, 53, 54, 56, 57, 63, 64, 65, 66.

Test Example 7

Insecticidal test on Maize weevil (*Sitophilus oryzae*)

A 5% emulsifiable concentrate (or a 25% wettable powder) of a compound of the present invention was diluted with water containing a spreader to give a 500 ppm solution of the compound.

Ten (10) g of unmilled rice in a laboratory dish were dipped with the obtained solution and air-dried, and then maize weevil adults each 10 of male and female were released therein. The laboratory dishes were kept in a thermostatic chamber.

Ninety (90) days after, evaluation was conducted by counting the number of the adults which came out.

The test was conducted twice of each compound.

As a result, no emerged adult was observed at all in the dishes treated with any one of the following compounds.

Compound Nos. 1, 2, 3, 4, 5, 6, 7, 8, 9, 10, 11, 20, 21, 31, 32, 34, 35, 36, 38, 42, 43, 44, 45, 46, 47, 56, 57, 63, 64, 65, 66.

Test Example 8

Insecticidal test on German cockroach (*Blattella germanica*)

In a transparent small test tube was weighed and placed 5% emulsifiable concentrate of a compound of the present invention (or a 25% wettable powder or a 20% oil solution thereof), and thereto was added acetone to give a 500 ppm acetone solution of the compound. Ten (10) cc of the acetone solution was added to 10 g of powder feed for small animals placed in a laboratory dish of 9 cm in diameter. After stirring, acetone was distilled away from the mixture. This laboratory dish was placed in a large laboratory dish of 20 cm in diameter to prepare a bait. In this large laboratory dish were released 10 five instar nymphae of German cockroaches (*Blattella germanica*). The large laboratory dish was kept in a thermostatic chamber. In the large laboratory dish, a laboratory dish containing moistured sanitary cotton was placed so as to give water to the nymphae.

Sixty (60) days after, evaluation was conducted by counting the number of the adults which came out.

The test was conducted twice of each compound.

As a result, no adult was observed at all in the dish treated with any one of the following compounds.

Compound Nos. 1, 2, 3, 4, 5, 6, 7, 8, 9, 10, 11, 19, 20, 21, 31, 32, 33, 34, 35, 36, 37, 38, 39, 40, 42, 43, 44, 45, 46, 47, 49, 50, 52, 53, 54, 56, 57.

Test Example 9

Insecticidal test on Housefly (*Musca domestica*)

A 5% emulsifiable concentrate (or a 25% wettable powder) of a compound of the present invention was diluted with water to give a 500 ppm solution of the compound.

One (1) cc of the solution was dropwise applied on a filter paper placed in a laboratory dish of 9 cm in diameter. Ten larvae of housefly (*Musca domestica*) were released in the dish. The dish containing the larvae was kept in a thermostatic chamber of 25 °C.

Two (2) weeks after, the number of the larvae killed was counted.

The test was conducted twice of each compound.

As a result, no emerged adult was observed at all in the dish treated with any one the following compounds. Compound Nos. 8, 9, 21, 42, 43, 45, 46, 47, 63, 65 27.

What is claimed is:

1. A compound of the formula (I)

$$\underset{\underset{R'}{|}}{\overset{R-N}{\underset{N}{\big|}}}\diagdown\diagup\overset{O}{\overset{\|}{C}}\diagdown\diagup\text{O}-J \quad (I)$$

wherein R represents an alkyl group having 1 to 4 carbon atoms substituted by a member selected from the group consisting of an unsubstituted phenyl group; and a phenyl group substituted by an alkyl group, a halogen atom, a trifluoromethyl group or a nitro group;

R' represents a hydrogen atom,

—J represents $$-CH_2-Q, \quad -\underset{|}{\overset{Rc}{C}}H-\underset{|}{\overset{Rd}{C}}HX-Q,$$

$$-\underset{|}{\overset{Rc}{C}}H\underset{|}{\overset{Rd}{C}}HX-CO-Rf \quad \text{or} \quad -\underset{|}{\overset{Rc}{C}}H\underset{|}{\overset{Rd}{C}}HX-CO_2-Rf,$$

wherein Rc and Rd independently represent a hydrogen atom or an alkyl group having 1 to 4 carbon atoms, Rf represents an alkyl group having 1 to 4 carbon atoms, an alkenyl group having 2 to 8 carbon atoms or a cycloalkyl group having 3 carbon atom;

X represents —O— or —NH—; and

Q represents an unsubstituted pyridyl group or a pyridyl group substituted by a halogen atom.

2. A compound according to claim 1 selected from the group consisting of:

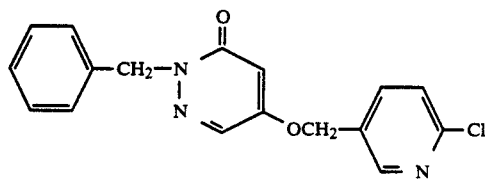

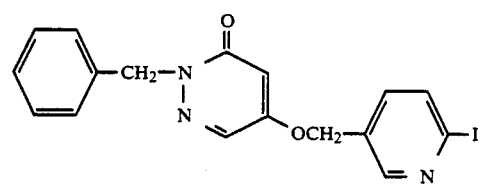

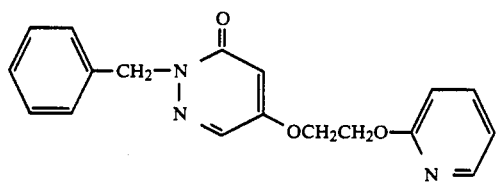

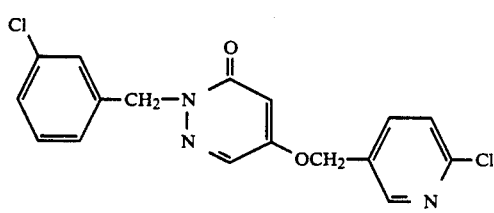

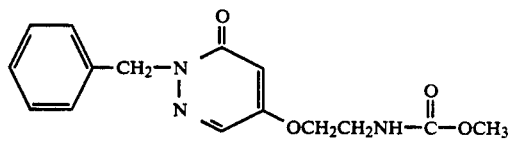

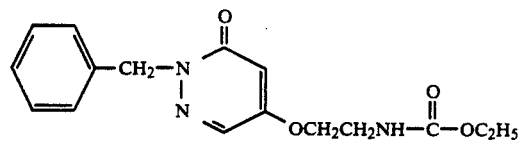

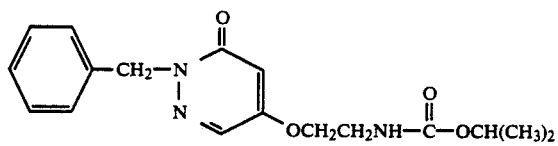

-continued

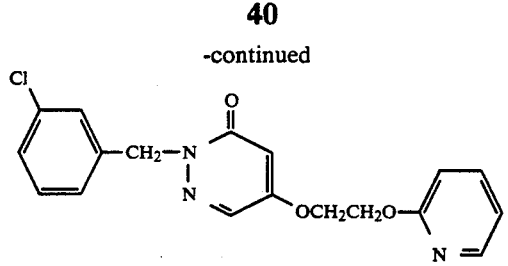

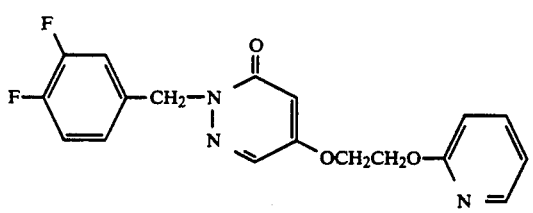

and

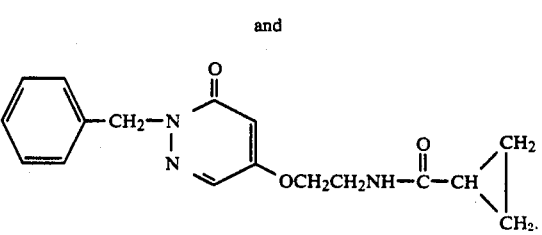

3. A composition for controlling and/or preventing infestation of pests selected from the group consisting of insects, acari, nematodes and mollusca, the composition containing as an active ingredient one or more compound of the formula (I) of claim 1.

4. A method for controlling and/or preventing infestation of pests selected from the group consisting of insects, acari, nematodes and mollusca, at a locus which comprises applying to said locus a pesticidally effective amount of one or more compound of the formula (I) of claim 1.

5. Method according to claim 4, wherein the pests to be controlled are insects and representatives of the order Acarina.

6. A method according to claim 4, wherein said one or more derivative is applied together with a carrier.

7. A compound of the formula (I)

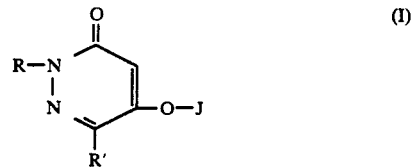

wherein R represents an alkyl group having 1 carbon atom substituted by a phenyl group which may be substituted by an alkyl group, a halogen atom, a trifluoromethyl group or a nitro group, R$^1$ represents a hydrogen atom, J represents

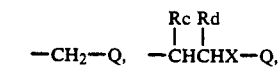

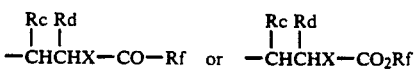

wherein Rc and Rd independently represent a hydrogen atom or a methyl group, Rf represents an alkyl group having 2 to 4 carbon atoms, an alkenyl group having 2 to 8 carbon atoms or a cycloalkyl group having 3 carbon atoms;

X represents —O— or —NH—; and

Q represents an unsubstituted pyridyl group or a pyridyl group substituted by a halogen atom.

8. A compound of the formula (I)

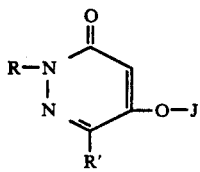

wherein R represents an alkyl group having 1 carbon atom substituted by a member selected from the group consisting of an unsubstituted phenyl group; and a phenyl group substituted by a halogen atom or a trifluoromethyl group, R' represents a hydrogen atom, J represents

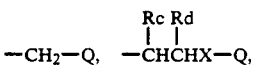

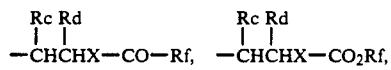

wherein Rc and Rd represent a hydrogen atom,

Rf represents an alkyl group having 1 to 4 carbon atoms or a cycloalkyl group having 3 carbon atoms, X represents —O—, or —NH—, and Q represents an unsubstituted pyridyl group or a pyridyl group substituted by a halogen atom.

9. A compound of the formula (I)

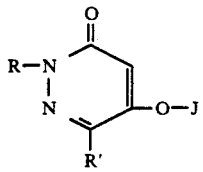

wherein R represents an alkyl group having 1 to 4 carbon atoms substituted by an unsubstituted phenyl group or a phenyl group substituted by an alkyl group, a halogen atom, a haloalkyl group or a nitro group, R¹ represents a hydrogen atom, J represents

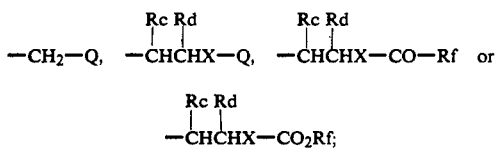

wherein:

Rc and Rd independently represent a hydrogen atom or an alkyl group having 1 to 4 carbon atoms, Rf represents a member selected from the group consisting of hydrogen atoms; an alkyl group having 1 to 4 carbon atoms; an alkenyl group having 2 to 8 carbon atoms; a cycloalkyl group having 3 carbon atoms; an unsubstituted phenyl group; and a phenyl group substituted by an alkyl group, a halogen atom, a haloalkyl group or a nitro group, X represents —O— or —NH—, and Q represents a substituted or unsubstituted pyridyl group.

10. A compound according to claim 8, wherein the substituted R phenyl is substituted by at least one methyl group, at least one halogen atom, a halo-substituted methyl group or a nitro group, and the substituted Rf phenyl is substituted by at least one methyl group, at least one halogen atom, a halo-substituted methyl group or a nitro group.

11. A compound according to claim 9, wherein the substituted R phenyl is substituted by at least one methyl group, at least one halogen atom, a halo-substituted methyl group or a nitro group, and the substituted Rf phenyl is substituted by at least one methyl group, at least one halogen atom, a halo-substituted methyl group or a nitro group.

12. A compound of the formula (I)

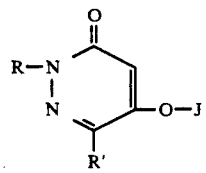

wherein R represents an alkyl group having 1 to 4 carbon atoms substituted by a substituted or unsubstituted phenyl group or a methyl group substituted by a pyridyl group, R' represents a hydrogen atom, J represents

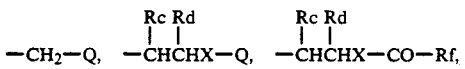

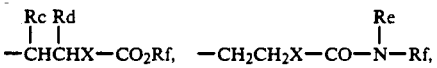

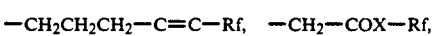

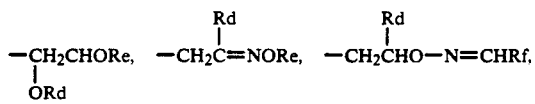

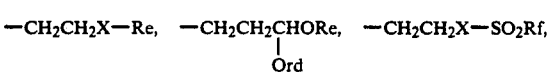

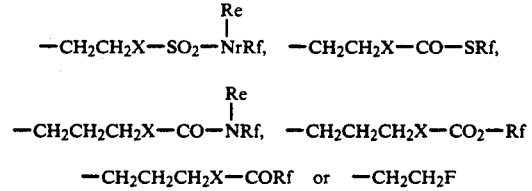

—CH₂CH₂CH₂X—CORf  or  —CH₂CH₂F wherein Rc, Rd and Re independently represent a hydrogen atom or an alkyl group having 1 to 4 carbon atoms, Rf represents a hydrogen atom, an alkyl group having 1 to 4 carbon atoms, an alkenyl group having 2 to 8 carbon atoms, a cycloalkyl group having 3 to 8 carbon atoms or a substituted or unsubstituted phenyl group;

X represents —O—, or —NH—,

Q represents a substituted or unsubstituted phenyl, pyridyl or pyridazyl group and said compound is selected from the group consisting of:

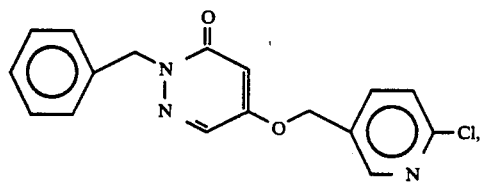

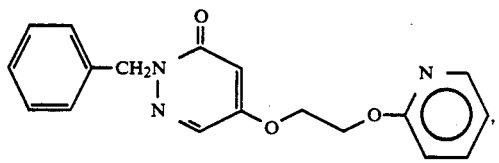

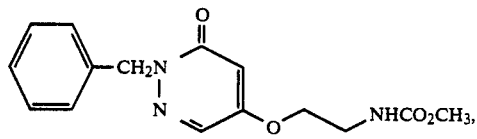

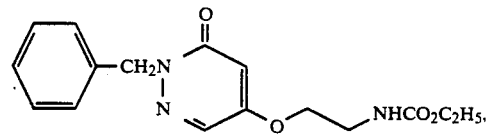

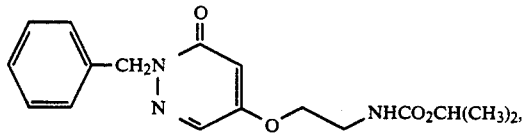

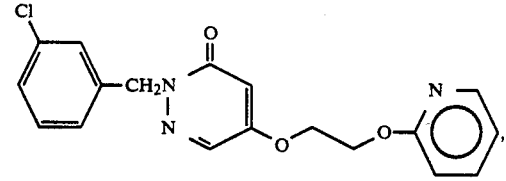

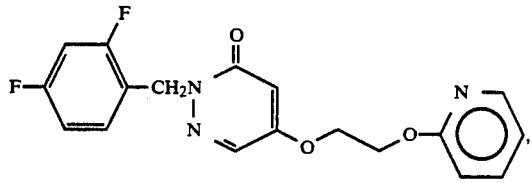

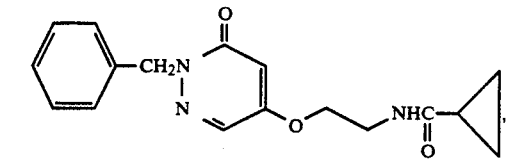

-continued

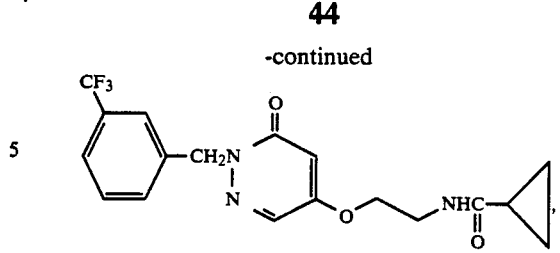

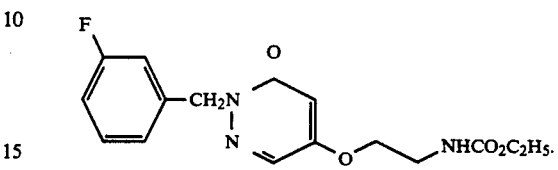

13. An insecticidal composition comprising a carrier and, as an active ingredient, an effective amount of a compound of the formula (I)

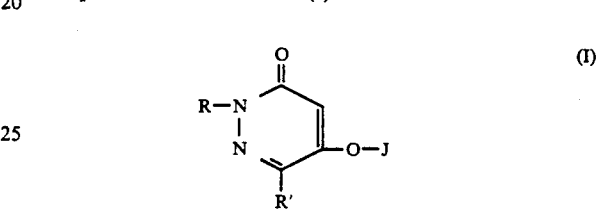

(I)

wherein R represents an alkyl group having 1 to 4 carbon atoms substituted by a member selected from the group consisting of an unsubstituted phenyl group; a phenyl group substituted by a member selected from the group consisting of an alkyl group; a halogen atom; a trifluoromethyl group and a nitro group, R' represents a hydrogen atom, J represents

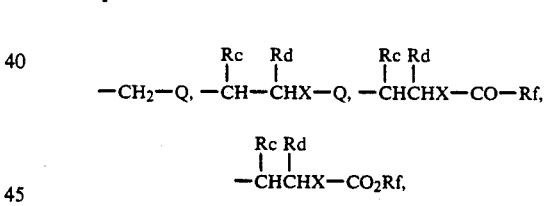

wherein Rc and Rd independently represent a hydrogen atom or an alkyl group having 1 to 4 carbon atoms, Rf represents an alkyl group having 1 to 4 carbon atoms, an alkenyl group having 2 to 8 carbon atoms or a cycloalkyl group having 3 carbon atoms; X represents —O— or —NH—; and Q represents an unsubstituted pyridyl group or a pyridyl group substituted halogen atom.

14. An insecticidal composition according to claim 13, wherein said compound is selected from the group consisting of:

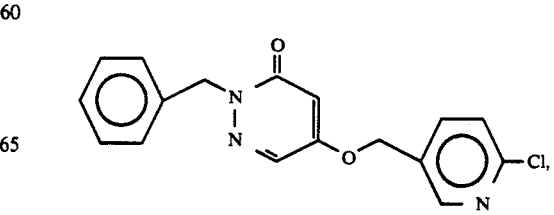

-continued

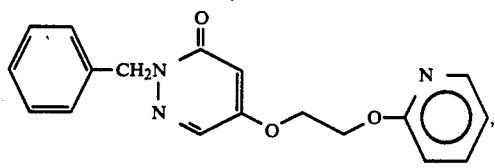

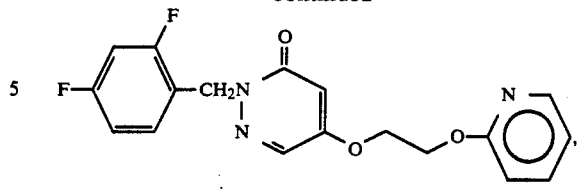

-continued

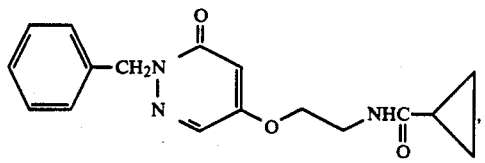

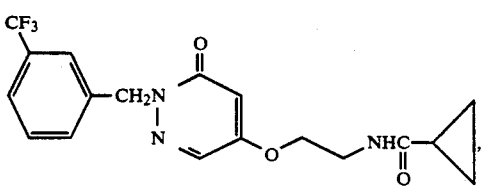

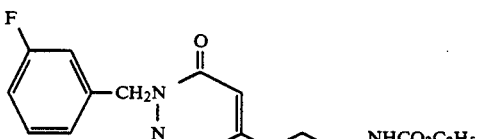

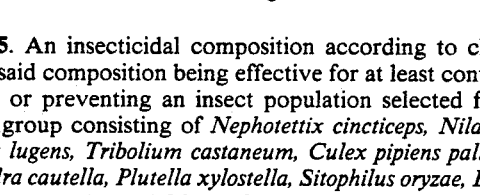

15. An insecticidal composition according to claim 13, said composition being effective for at least controlling or preventing an insect population selected from the group consisting of *Nephotettix cincticeps, Nilaparvata lugens, Tribolium castaneum, Culex pipiens pallens, Cadra cautella, Plutella xylostella, Sitophilus oryzae, Blattella germanica* and *Musca domestica*.

* * * * *